US006949545B2

(12) United States Patent
Pikul et al.

(10) Patent No.: US 6,949,545 B2
(45) Date of Patent: Sep. 27, 2005

(54) HETEROCYCLIC SIDE CHAIN CONTAINING, N-SUBSTITUTED METALLOPROTEASE INHIBITORS

(75) Inventors: Stanislaw Pikul, Germantown, MD (US); Norman Eugene Ohler, New Market, MD (US); Neil Gregory Almstead, Holmdel, NJ (US); Steven Karl Laughlin, Independence, KY (US); Michael George Natchus, Alpharetta, GA (US); Biswanath De, Cincinnati, OH (US); Paul Mitchell Hershberger, Maineville, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 361 days.

(21) Appl. No.: 10/243,511

(22) Filed: Sep. 13, 2002

(65) Prior Publication Data

US 2003/0139414 A1 Jul. 24, 2003

Related U.S. Application Data

(63) Continuation-in-part of application No. PCT/US01/08931, filed on Mar. 20, 2001
(60) Provisional application No. 60/191,302, filed on Mar. 21, 2000.

(51) Int. Cl.$^7$ ............... A61K 31/5377; A61P 19/02; C07D 211/06; C07D 413/012
(52) U.S. Cl. ............... 514/237.2; 514/330; 544/130; 546/194; 546/221; 546/227; 546/234
(58) Field of Search ............... 544/130; 546/194, 546/221, 227; 514/237.2

(56) References Cited

U.S. PATENT DOCUMENTS

| | | |
|---|---|---|
| 4,743,587 A | 5/1988 | Dickens et al. |
| 4,771,038 A | 9/1988 | Wolanin et al. |
| 4,885,283 A | 12/1989 | Broadhurst et al. |
| 4,996,358 A | 2/1991 | Handa et al. |
| 5,006,651 A | 4/1991 | Broadhurst et al. |
| 5,183,900 A | 2/1993 | Galardy et al. |
| 5,300,674 A | 4/1994 | Crimmin et al. |
| 5,318,964 A | 6/1994 | Broadhurst et al. |
| 5,326,760 A | 7/1994 | McElroy et al. |
| 5,387,610 A | 2/1995 | Gray et al. |
| 5,403,952 A | 4/1995 | Hagmann et al. |
| 5,412,145 A | 5/1995 | Crimmin et al. |
| 5,442,110 A | 8/1995 | Isomura et al. |
| 5,447,929 A | 9/1995 | Broadhurst et al. |
| 5,470,834 A | 11/1995 | Schwartz et al. |
| 5,473,100 A | 12/1995 | Isomura et al. |
| 5,506,242 A | 4/1996 | MacPherson et al. |
| 5,514,716 A | 5/1996 | Gowravaram et al. |
| 5,545,735 A | 8/1996 | Bochis et al. |
| 5,614,625 A | 3/1997 | Broadhurst et al. |
| 5,616,605 A | 4/1997 | Gray et al. |
| 5,618,844 A | 4/1997 | Gowravaram et al. |
| 5,646,167 A | 7/1997 | MacPherson et al. |
| 5,665,753 A | 9/1997 | Frazee et al. |
| 5,691,382 A | 11/1997 | Crimmin et al. |
| 5,698,690 A | 12/1997 | Broadhurst et al. |
| 5,710,167 A | 1/1998 | Broadhurst et al. |
| 5,714,491 A | 2/1998 | Morphy et al. |
| 5,731,441 A | 3/1998 | Broadhurst et al. |
| 5,747,514 A | 5/1998 | Beckett et al. |
| 5,763,621 A | 6/1998 | Beckett et al. |
| 5,773,438 A | 6/1998 | Levy et al. |
| 5,827,890 A | 10/1998 | Beeley et al. |
| 5,853,623 A | 12/1998 | Montana et al. |
| 5,859,253 A | 1/1999 | Beckett et al. |

(Continued)

FOREIGN PATENT DOCUMENTS

| | | |
|---|---|---|
| EP | 0 606 046 A1 | 7/1994 |
| EP | 0 575 844 B1 | 1/1998 |

(Continued)

OTHER PUBLICATIONS

J. Nemunaitis, et al., "Combined Analysis of Studies of the Effects of the Matrix Metalloproteinase Inhibitor Marimastat on Serum Tumor Markers in Advanced Cancer: Selection of a Biologically Active and Tolerable Dose for Longerterm Studies", *Clinical Cancer Research*, vol. 4, pp. 1101–1109 (1998).

(Continued)

*Primary Examiner*—Laura L. Stockton
(74) *Attorney, Agent, or Firm*—Mary Pat McMahon; David V. Upite; Andrew A. Paul

(57) ABSTRACT

Disclosed are compounds which are inhibitors of metalloproteases and which are effective in treating conditions characterized by excess activity of these enzymes. In particular, the compounds have a structure according to the following Formula (I):

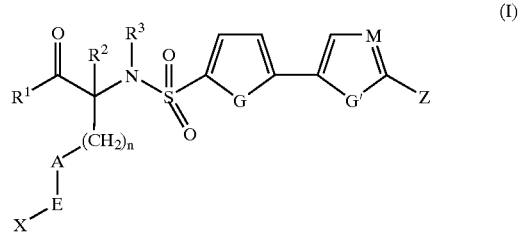

where $R^1$, $R^2$, $R^3$, n, A, E, X, G, G', M and Z have the meanings described in the specification and the claims, as well as optical isomers, diastereomers and enantiomers of Formula I, and pharmaceutically-acceptable salts, biohydrolyzable amides, esters, and imides thereof. Also described are pharmaceutical compositions comprising these compounds, and methods of treating metalloprotease-related maladies using the compounds or the pharmaceutical compositions.

22 Claims, No Drawings

U.S. PATENT DOCUMENTS

| | | | |
|---|---|---|---|
| 5,861,436 | A | 1/1999 | Beckett et al. |
| 5,872,152 | A | 2/1999 | Brown et al. |
| 5,886,022 | A | 3/1999 | Kluender et al. |
| 5,892,112 | A | 4/1999 | Levy et al. |
| 5,902,791 | A | 5/1999 | Beckett et al. |
| 5,919,940 | A | 7/1999 | Martin |
| 5,962,529 | A | 10/1999 | Miller et al. |
| 6,017,889 | A | 1/2000 | Beckett et al. |
| 6,022,898 | A | 2/2000 | Miller et al. |
| 6,028,110 | A | 2/2000 | Miller et al. |
| 6,066,662 | A | 5/2000 | Broadhurst et al. |
| 6,093,398 | A | 7/2000 | Khaw et al. |
| 6,114,435 | A * | 9/2000 | Nilz et al. ............... 524/548 |
| 6,124,329 | A | 9/2000 | Miller et al. |
| 6,124,332 | A | 9/2000 | Miller et al. |
| 6,124,333 | A | 9/2000 | Miller et al. |
| 6,166,082 | A | 12/2000 | Kluender et al. |
| 6,225,311 | B1 | 5/2001 | Levin et al. |
| 6,239,288 | B1 | 5/2001 | Purchase, Jr. et al. |
| 6,307,089 | B2 | 10/2001 | Purchase, Jr. et al. |
| 6,379,667 | B1 | 4/2002 | Khaw et al. |
| 6,407,235 | B1 * | 6/2002 | Alanine et al. ............ 544/130 |
| 2001/0000513 | A1 | 4/2001 | Purchase, Jr. et al. |
| 2002/0164319 | A1 | 11/2002 | Khaw et al. |

FOREIGN PATENT DOCUMENTS

| | | |
|---|---|---|
| EP | 0 877 018 A1 | 11/1998 |
| EP | 0 895 988 A1 | 2/1999 |
| EP | 0 950 656 A1 | 10/1999 |
| EP | 0 979 816 A1 | 2/2000 |
| GB | 2 268 934 A | 1/1994 |
| JP | 07-304770 | 11/1995 |
| JP | 08-053403 | 2/1996 |
| WO | WO 92/17460 | 10/1992 |
| WO | WO 93/14112 | 7/1993 |
| WO | WO 94/25435 | 11/1994 |
| WO | WO 95/12603 | 5/1995 |
| WO | WO 95/29892 | 11/1995 |
| WO | WO 95/33731 | 12/1995 |
| WO | WO 96/00214 | 1/1996 |
| WO | WO 97/22587 | 6/1997 |
| WO | WO 98/33768 | 8/1998 |
| WO | WO 98/39329 | 9/1998 |
| WO | WO 99/06340 | 2/1999 |
| WO | WO 99/18079 | 4/1999 |
| WO | WO 99/42443 | 8/1999 |
| WO | WO 99/52889 | 10/1999 |
| WO | WO 00/51993 A3 | 9/2000 |
| WO | WO 00/51993 | 9/2000 |
| WO | WO 00/73294 A2 | 12/2000 |
| WO | WO 00/73295 A1 | 12/2000 |

OTHER PUBLICATIONS

A. E. Yu, et al., "Matrix Metalloproteinases—Novel Targets for Directed Cancer Therapy", *Drugs and Aging*, vol. 11, No. 3, pp. 229–244 (1997).

J. Bird, et al., "Synthesis of Novel N–Phosphonoalkyl Dipeptide Inhibitors of Human Collaganase", *Journal of Medicinal Chemistry*, vol. 37, No. 1, pp. 158–169 (1994).

K. Gijbels, et al., "Reversal of Experimental Autoimmune Encephalomyelitis with a Hydroxamate Inhibitor of Matrix Metalloproteases", *J. Clin. Invest.*, vol. 94, pp. 2177–2182 (1994).

B. Henderson, et al., "Design of Inhibitors of Articular Cartilage Destruction", *Drugs of the Future*, vol. 15, No. 5, pp. 495–508 (1990).

A. F. Chambers, et al., "Changing Views of the Role of Matrix Metalloproteinases in Metastasis", *Journal of the National Cancer Institute*, vol. 89, No. 17, pp. 1260–1270 (1997).

R. Reich, et al., "Effects of Inhibitors of Plasminogen Activator, Serine Proteinases, and Collagenase IV on the Invasion of Basement Membranes by Metastatic Cells" *Cancer Research*, vol. 48, pp. 3307–3312 (1988).

T. G. Wolfsberg, et al., "ADAM, a Novel Family of Membrane Proteins Containg A Disintegrin And Metalloprotease Domain: Multipotential Functions in Cell–Cell and CellMatrix Interactions", *The Journal of Cell Biology*, vol. 131, No. 2, pp. 275–278 (1995).

H. S. Rasmussen, et al., "Matrix Metalloproteinase Inhibition as a Novel Anticancer Strategy: A Review with Special Focus on Batimastat and Marimastat", *Pharmacol. Th r.*, vol. 75, No. 1, pp. 69–75 (1997).

D. E. Mullins, et al., "The Role of Proteinases in Cellular Invasiveness", *Biochimica et Biophysica Acta.*, vol. 695, pp. 177–214 (1983).

S. R. Bramhall, "The Matrix Metalloproteinases and Their Inhibitors in Pancreatic Cancer", *International Journal of Pancreatology*, vol. 21, No. 1, pp. 1–12 (1997).

J. R. Morphy, et al. "Matrix Metalloproteinase Inhibitors: Current Status", *Current Medicinal Chemistry*, vol. 2, pp. 743–762 (1995).

* cited by examiner

HETEROCYCLIC SIDE CHAIN CONTAINING, N-SUBSTITUTED METALLOPROTEASE INHIBITORS

CROSS REFERENCE

This application is a continuation in part under 35 USC § 120 of International Application PCT/US01/08931, with an international filing date of Mar. 20, 2001 and which claims benefit of 35 United States Code § 119(e) of Provisional Application Ser. No. 60/191,302 filed Mar. 21, 2000.

TECHNICAL FIELD

This invention is directed to compounds which are useful in treating diseases associated with metalloprotease activity, particularly zinc metalloprotease activity. The invention is also directed to pharmaceutical compositions comprising the compounds, and to methods of treating metalloprotease-related maladies using the compounds or the pharmaceutical compositions.

BACKGROUND

A number of structurally related metalloproteases effect the breakdown of structural proteins. These metalloproteases often act on the intercellular matrix, and thus are involved in tissue breakdown and remodeling. Such proteins are referred to as metalloproteases or MPs.

There are several different families of MPs, classified by sequence homology, disclosed in the art. These MPs include Matrix-Metallo Proteases (MMPs); zinc metalloproteases; many of the membrane bound metalloproteases; TNF converting enzymes; angiotensin-converting enzymes (ACEs); disintegrins, including ADAMs (see Wolfsberg et al, 131 *J. Cell Bio.* 275–78 October, 1995); and the enkephalinases. Examples of MPs include human skin fibroblast collagenase, human skin fibroblast gelatinase, human sputum collagenase, aggrecanse and gelatinase, and human stromelysin. Collagenases, stromelysin, aggrecanase and related enzymes are thought to be important in mediating the symptomatology of a number of diseases.

Potential therapeutic indications of MP inhibitors have been discussed in the literature. See, for example, U.S. Pat. Nos. 5,506,242 (Ciba Geigy Corp.) and 5,403,952 (Merck & Co.); the following PCT published applications: WO 96/06074 (British Bio Tech Ltd.); WO 96/00214 (Ciba Geigy), WO 95/35275 (British Bio Tech Ltd.), WO 95/35276 (British Bio Tech Ltd.), WO 95/33731 (Hoffman-LaRoche), WO 95/33709 (Hoffman-LaRoche), WO 95/32944 (British Bio Tech Ltd.), WO 95/26989 (Merck), WO 9529892 (DuPont Merck), WO 95/24921 (Inst. Opthamology), WO 95/23790 (SmithKline Beecham), WO 95/22966 (Sanofi Winthrop), WO 95/19965 (Glycomed), WO 95 19956 (British Bio Tech Ltd), WO 95/19957 (British Bio Tech Ltd.), WO 95/19961 (British Bio Tech Ltd.), WO 95/13289 (Chiroscience Ltd.), WO 95/12603 (Syntex), WO 95/09633 (Florida State Univ.), WO 95/09620 (Florida State Univ.), WO 95/04033 (Celltech), WO 94/25434 (Celltech), WO 94/25435 (Celltech); WO 93/14112 (Merck), WO 94/0019 (Glaxo), WO 93/21942 (British Bio Tech Ltd.), WO 92/22523 (Res. Corp. Tech Inc.), WO 94/10990 (British Bio Tech Ltd.), WO 93/09090 (Yamanouchi); British patents GB 2282598 (Merck) and GB 2268934 (British Bio Tech Ltd.); published European Patent Applications EP 95/684240 (Hoffman LaRoche), EP 574758 (Hoffman LaRoche) and EP 575844 (Hoffman LaRoche); published Japanese applications JP 08053403 (Fujusowa Pharm. Co. Ltd.) and JP 7304770 (Kanebo Ltd.); and Bird et al., *J. Med. Chem.*, vol. 37, pp. 158–69 (1994).

Examples of potential therapeutic uses of MP inhibitors include rheumatoid arthritis—Mullins, D. E., et al., *Biochim. Biophys. Acta.* (1983) 695:117–214; osteoarthritis—Henderson, B., et al., *Drugs of the Future* (1990) 15:495–508; cancer—Yu, A. E. et al., *Matrix Metalloproteinases—Novel Targets for Directed Cancer Therapy*, Drugs & Aging, Vol. 11(3), p. 229–244 (September 1997), Chambers, A. F. and Matrisian, L. M., *Review: Changing Views of the Role of Matrix Metalloproteinases in Metastasis*, J. of the Nat'l Cancer Inst., Vol. 89(17), p. 1260–1270 (September 1997), Bramhall, S. R., *The Matrix Metalloproteinases and Their Inhibitors in Pancreatic Cancer,* Internat'l J. of Pancreatology, Vol. 4, p. 1101–1109 (May 1998), Nemunaitis, J. et al., *Combined Analysis of Studies of the Effects of the Matrix Metalloproteinase Inhibitor Marimastat on Serum Tumor Markers in Advanced Cancer: Selection of a Biologically Active and Tolerable Dose for Longer-term Studies, Clin. Cancer Res.*, Vol 4, p. 1101–1109 (May 1998), and Rasmussen, H. S. and McCann, P. P, *Matrix Metalloproteinase Inhibition as a Novel Anticancer Strategy: A Review with Special Focus on Batimastat and Marimastat, Pharmacol. Ther.*, Vol 75(1), p. 69–75 (1997); the metastasis of tumor cells—ibid, Broadhurst, M. J., et al., European Patent Application 276,436 (published 1987), Reich, R., et al., *Cancer Res.*, Vol. 48, p. 3307–3312 (1988); multiple sclerosis—Gijbels et al., *J. Clin. Invest.*, vol. 94, p. 2177–2182 (1994); and various ulcerations or ulcerative conditions of tissue. For example, ulcerative conditions can result in the cornea as the result of alkali burns or as a result of infection by *Pseudomonas aeruginosa*, Acanthamoeba, Herpes simplex and vaccinia viruses. Other examples of conditions characterized by undesired metalloprotease activity include periodontal disease, epidermolysis bullosa, fever, inflammation and scleritis (e.g., DeCicco et al., PCT published application WO 95/29892, published Nov. 9, 1995).

In view of the involvement of such metalloproteases in a number of disease conditions, attempts have been made to prepare inhibitors to these enzymes. A number of such inhibitors are disclosed in the literature. Examples include U.S. Pat. No. 5,183,900, issued Feb. 2, 1993 to Galardy; U.S. Pat. No. 4,996,358, issued Feb. 26, 1991 to Handa et al.; U.S. Pat. No. 4,771,038, issued Sep. 13, 1988 to Wolanin et al.; U.S. Pat. No. 4,743,587, issued May 10, 1988 to Dickens et al., European Patent Publication No. 575,844, published Dec. 29, 1993 by Broadhurst et al.; International Patent Publication No. WO 93/09090, published May 13, 1993 by Isomura et al.; World Patent Publication 92/17460, published Oct. 15, 1992 by Markwell et al.; and European Patent Publication No. 498,665, published Aug. 12, 1992 by Beckett et al.

It would be advantageous to inhibit these metalloproteases in treating diseases related to unwanted metalloprotease activity. Though a variety of MP inhibitors have been prepared, there is a continuing need for potent matrix metalloprotease inhibitors useful in treating diseases associated with metalloprotease activity.

SUMMARY OF THE INVENTION

The invention provides compounds which are potent inhibitors of metalloproteases and which are effective in treating conditions characterized by excess activity of these enzymes. In particular, the present invention relates to compounds having a structure according to Formula (I):

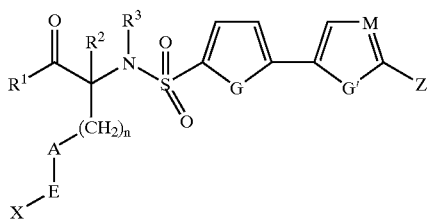

wherein:
(A) $R^1$ is selected from —OH and —NHOH;
(B) $R^2$ is selected from hydrogen, alkyl, alkenyl, alkynyl, heteroalkyl, haloalkyl, cycloalkylalkyl, heterocycloalkylalkyl, arylalkyl and heteroarylalkyl; or $R^2$ can be connected to A as described in (D);
(C) $R^3$ is selected from alkyl, alkenyl, alkynyl, heteroalkyl, haloalkyl, cycloalkyl, heterocycloalkyl, arylalkyl and heteroarylalkyl;
(D) A is a substituted or unsubstituted, monocyclic heterocycloalkyl having from 3 to 8 ring atoms of which 1 to 3 are heteroatoms; or A is bonded to $R^2$ where, together, they form a substituted or unsubstituted, monocyclic heterocycloalkyl having from 3 to 8 ring atoms of which 1 to 3 are heteroatoms;
(E) n is from 0 to about 4;
(F) E is selected from a covalent bond, $C_1$–$C_4$ alkyl, —C(=O)—, —C(=O)O—, C(=O)N($R^4$)—, —$SO_2$—, or —C(=S)N($R^4$)—, where $R^4$ is selected from hydrogen, alkyl, alkenyl, alkynyl, heteroalkyl, haloalkyl, cycloalkyl, heterocycloalkyl, aryl, arylalkyl, heteroaryl and heteroarylalkyl; or $R^4$ and X join to form a ring as described in (G)(2);
(G) (1) X is selected from hydrogen, alkyl, alkenyl, alkynyl, heteroalkyl, haloalkyl, aryl, arylalkyl, heteroaryl, heteroarylalkyl, cycloalkyl and heterocycloalkyl; or (2) X and $R^4$ join to form a substituted or unsubstituted, monocyclic heterocycloalkyl having from 3 to 8 ring atoms of which 1 to 3 are heteroatoms;
(H) G is selected from —S—, —O—, —N($R^5$)—, —C($R^5$)=C($R^5$)—, —N=C($R^5$)—, and —N=N—, where $R^5$ and $R^{5'}$ each is independently selected from hydrogen, alkyl, alkenyl, alkynyl, heteroalkyl, aryl, heteroaryl, cycloalkyl and heterocycloalkyl;
(I) G' is selected from —S—, —O—, —N($R^6$)—, —C($R^6$)=C($R^6$)—, —N=C($R^6$)—, and —N=N— where $R^6$ and $R^{6'}$ each is independently selected from hydrogen, alkyl, alkenyl, alkynyl, heteroalkyl, aryl, heteroaryl, cycloalkyl and heterocycloalkyl;
(J) M is selected from —CH— and —N—; and
(K) Z is —$(CR^1R^7)_a$—L—$R^8$, where:
  (1) a is from 0 to about 4;
  (2) each $R^7$ and $R^{7'}$ is independently selected from hydrogen, alkyl, alkenyl, alkynyl, aryl, heteroalkyl, heteroaryl, cycloalkyl, heterocycloalkyl, halogen, haloalkyl, hydroxy and alkoxy;
  (3) L is nil or a connecting group selected from a covalent bond, —O—, —$SO_b$—, —C(=O)—, —C(=O)N($R^9$)—, —N($R^9$)— and —N($R^9$)C(=O)—; where b is from 0 to 2 and $R^9$ is selected from hydrogen, alkyl, alkenyl, alkynyl, aryl, heteroaryl, heteroalkyl, heteroaryl, cycloalkyl, heterocycloalkyl and haloalkyl; or $R^7$ and $R^9$, together with the atoms to which they are bonded, join to form an optionally substituted heterocyclic ring containing from 5 to 8 atoms of which 1 to 3 are heteroatoms; and
  (4) $R^8$ is selected from hydrogen, alkyl, alkenyl, alkynyl, halogen, heteroalkyl, haloalkyl, aryl, heteroaryl, cycloalkyl and heterocycloalkyl; or $R^8$ and $R^9$, together with the atoms to which they are bonded, join to form an optionally substituted heterocyclic ring containing from 5 to 8 atoms of which 1 to 3 are heteroatoms;

or an optical isomer, diastereomer or enantiomer for Formula (I), or a pharmaceutically-acceptable salt, or biohydrolyzable amide, ester, or imide thereof.

This invention also includes optical isomers, diastereomers and enantiomers of the formula above, and pharmaceutically-acceptable salts, biohydrolyzable amides, esters, and imides thereof.

The compounds of the present invention are useful for the treatment of diseases and conditions which are characterized by unwanted metalloprotease activity. Accordingly, the invention further provides pharmaceutical compositions comprising these compounds. The invention still further provides methods of treatment for metalloprotease-related maladies.

DETAILED DESCRIPTION OF THE INVENTION

I. Terms and Definitions:
The following is a list of definitions for terms used herein:
The following is a list of definitions for terms used herein.
"Acyl" or "carbonyl" is a radical formed by removal of the hydroxy from a carboxylic acid (i.e., R—C(=O)—). Preferred acyl groups include (for example) acetyl, formyl, and propionyl.

"Alkyl" is a saturated hydrocarbon chain having 1 to 15 carbon atoms, preferably 1 to 10, more preferably 1 to 4 carbon atoms. "Alkene" is a hydrocarbon chain having at least one (preferably only one) carbon-carbon double bond and having 2 to 15 carbon atoms, preferably 2 to 10, more preferably 2 to 4 carbon atoms. "Alkyne" is a hydrocarbon chain having at least one (preferably only one) carbon-carbon triple bond and having 2 to 15 carbon atoms, preferably 2 to 10, more preferably 2 to 4 carbon atoms. Alkyl, alkene and alkyne chains (referred to collectively as "hydrocarbon chains") may be straight or branched and may be unsubstituted or substituted. Preferred branched alkyl, alkene and alkyne chains have one or two branches, preferably one branch. Preferred chains are alkyl. Alkyl, alkene and alkyne hydrocarbon chains each may be unsubstituted or substituted with from 1 to 4 substituents; when substituted, preferred chains are mono-, di-, or tri-substituted. Alkyl, alkene and alkyne hydrocarbon chains each may be substituted with halo, hydroxy, aryloxy (e.g., phenoxy), heteroaryloxy, acyloxy (e.g., acetoxy), carboxy, aryl (e.g., phenyl), heteroaryl, cycloalkyl, heterocycloalkyl, spirocycle, amino, amido, acylamino, keto, thioketo, cyano, or any combination thereof. Preferred hydrocarbon groups include methyl, ethyl, propyl, isopropyl, butyl, vinyl, allyl, butenyl, and exomethylenyl.

Also, as referred to herein, a "lower" alkyl, alkene or alkyne moiety (e.g., "lower alkyl") is a chain comprised of 1 to 6, preferably from 1 to 4, carbon atoms in the case of alkyl and 2 to 6, preferably 2 to 4, carbon atoms in the case of alkene and alkyne.

"Alkoxy" is an oxygen radical having a hydrocarbon chain substituent, where the hydrocarbon chain is an alkyl or alkenyl (i.e., —O-alkyl or —O-alkenyl). Preferred alkoxy groups include (for example) methoxy, ethoxy, propoxy and allyloxy.

"Aryl" is an aromatic hydrocarbon ring. Aryl rings are monocyclic or fused bicyclic ring systems. Monocyclic aryl rings contain 6 carbon atoms in the ring. Monocyclic aryl rings are also referred to as phenyl rings. Bicyclic aryl rings contain from 8 to 17 carbon atoms, preferably 9 to 12 carbon atoms, in the ring. Bicyclic aryl rings include ring systems wherein one ring is aryl and the other ring is aryl, cycloalkyl, or heterocycloakyl. Preferred bicyclic aryl rings comprise 5-, 6- or 7-membered rings fused to 5-, 6-, or 7-membered rings. Aryl rings may be unsubstituted or substituted with from 1 to 4 substituents on the ring. Aryl may be substituted with halo, cyano, nitro, hydroxy, carboxy, amino, acylamino, alkyl, heteroalkyl, haloalkyl, phenyl, aryloxy, alkoxy, heteroalkyloxy, carbamyl, haloalkyl, methylenedioxy, heteroaryloxy, or any combination thereof. Preferred aryl rings include naphthyl, tolyl, xylyl, and phenyl. The most preferred aryl ring radical is phenyl.

"Aryloxy" is an oxygen radical having an aryl substituent (i.e., —O-aryl). Preferred aryloxy groups include (for example) phenoxy, napthyloxy, methoxyphenoxy, and methylenedioxyphenoxy.

"Cycloalkyl" is a saturated or unsaturated hydrocarbon ring. Cycloalkyl rings are not aromatic. Cycloalkyl rings are monocyclic, or are fused, spiro, or bridged bicyclic ring systems. Monocyclic cycloalkyl rings contain from about 3 to about 9 carbon atoms, preferably from 3 to 7 carbon atoms, in the ring. Bicyclic cycloalkyl rings contain from 7 to 17 carbon atoms, preferably from 7 to 12 carbon atoms, in the ring. Preferred bicyclic cycloalkyl rings comprise 4-, 5-, 6- or 7-membered rings fused to 5-, 6-, or 7-membered rings. Cycloalkyl rings may be unsubstituted or substituted with from 1 to 4 substituents on the ring. Cycloalkyl may be substituted with halo, cyano, alkyl, heteroalkyl, haloalkyl, phenyl, keto, hydroxy, carboxy, amino, acylamino, aryloxy, heteroaryloxy, or any combination thereof. Preferred cycloalkyl rings include cyclopropyl, cyclopentyl, and cyclohexyl.

"Halo" or "halogen" is fluoro, chloro, bromo or iodo. Preferred halo are fluoro, chloro and bromo; more preferred typically are chloro and fluoro, especially fluoro.

"Haloalkyl" is a straight, branched, or cyclic hydrocarbon substituted with one or more halo substituents. Preferred are $C_1$–$C_{12}$ haloalkyls; more preferred are $C_1$–$C_6$ haloalkyls; still more preferred still are $C_1$–$C_3$ haloalkyls. Preferred halo substituents are fluoro and chloro. The most preferred haloalkyl is trifluoromethyl.

"Heteroatom" is a nitrogen, sulfur, or oxygen atom. Groups containing more than one heteroatom may contain different heteroatoms.

"Heteroalkyl" is a saturated or unsaturated chain containing carbon and at least one heteroatom, wherein no two heteroatoms are adjacent. Heteroalkyl chains contain from 2 to 15 member atoms (carbon and heteroatoms) in the chain, preferably 2 to 10, more preferably 2 to 5. For example, alkoxy (i.e., —O-alkyl or —O-heteroalkyl) radicals are included in heteroalkyl. Heteroalkyl chains may be straight or branched. Preferred branched heteroalkyl have one or two branches, preferably one branch. Preferred heteroalkyl are saturated. Unsaturated heteroalkyl have one or more carbon-carbon double bonds and/or one or more carbon-carbon triple bonds. Preferred unsaturated heteroalkyls have one or two double bonds or one triple bond, more preferably one double bond. Heteroalkyl chains may be unsubstituted or substituted with from 1 to 4 substituents. Preferred substituted heteroalkyl are mono-, di-, or tri-substituted. Heteroalkyl may be substituted with lower alkyl, haloalkyl, halo, hydroxy, aryloxy, heteroaryloxy, acyloxy, carboxy, monocyclic aryl, heteroaryl, cycloalkyl, heterocycloalkyl, spirocycle, amino, acylamino, amido, keto, thioketo, cyano, or any combination thereof.

"Heteroaryl" is an aromatic ring containing carbon atoms and from 1 to about 6 heteroatoms in the ring. Heteroaryl rings are monocyclic or fused bicyclic ring systems. Monocyclic heteroaryl rings contain from about 5 to about 9 member atoms (carbon and heteroatoms), preferably 5 or 6 member atoms, in the ring. Bicyclic heteroaryl rings contain from 8 to 17 member atoms, preferably 8 to 12 member atoms, in the ring. Bicyclic heteroaryl rings include ring systems wherein one ring is heteroaryl and the other ring is aryl, heteroaryl, cycloalkyl, or heterocycloalkyl. Preferred bicyclic heteroaryl ring systems comprise 5-, 6- or 7-membered rings fused to 5-, 6-, or 7-membered rings. Heteroaryl rings may be unsubstituted or substituted with from 1 to 4 substituents on the ring. Heteroaryl may be substituted with halo, cyano, nitro, hydroxy, carboxy, amino, acylamino, alkyl, heteroalkyl, haloalkyl, phenyl, alkoxy, aryloxy, heteroaryloxy, or any combination thereof. Preferred heteroaryl rings include, but are not limited to, the following:

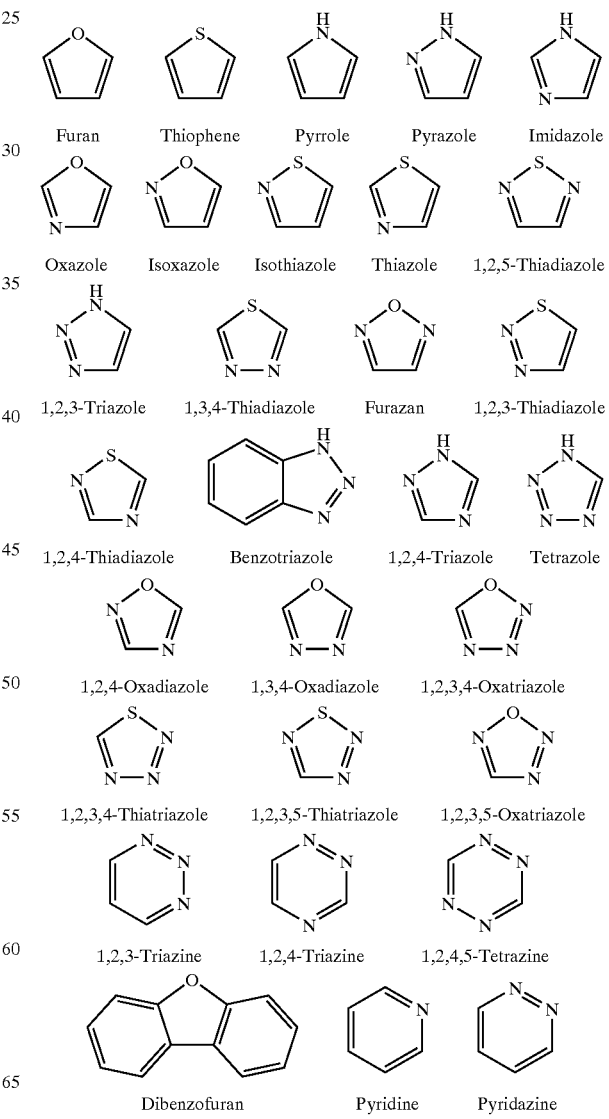

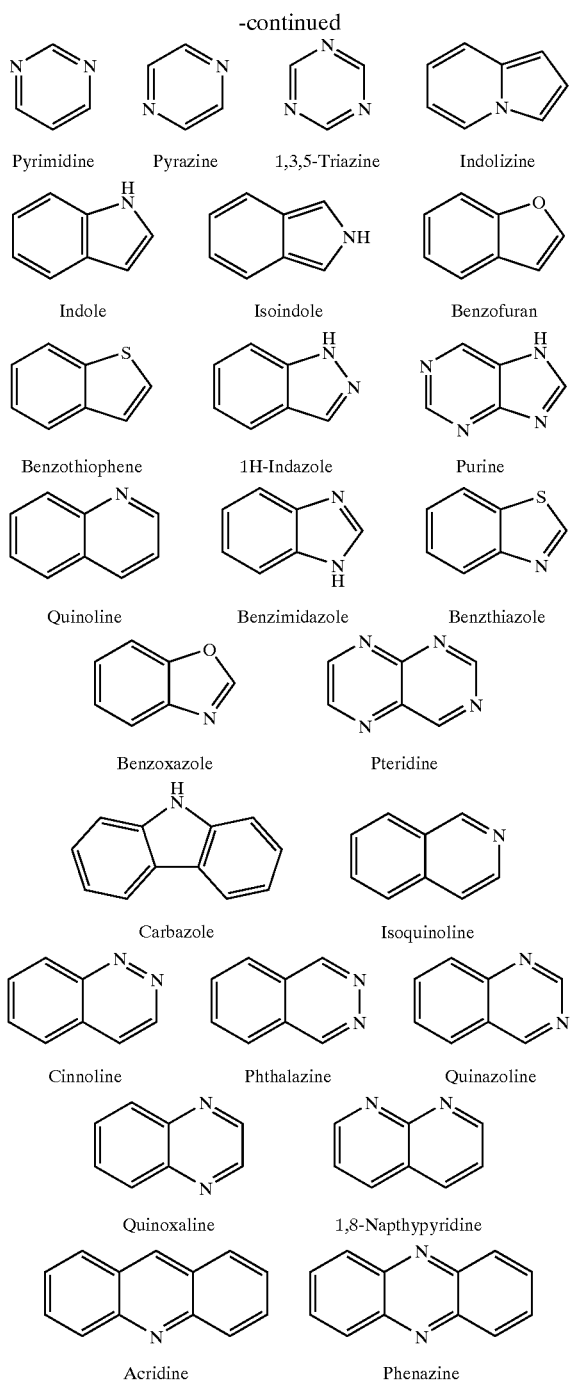

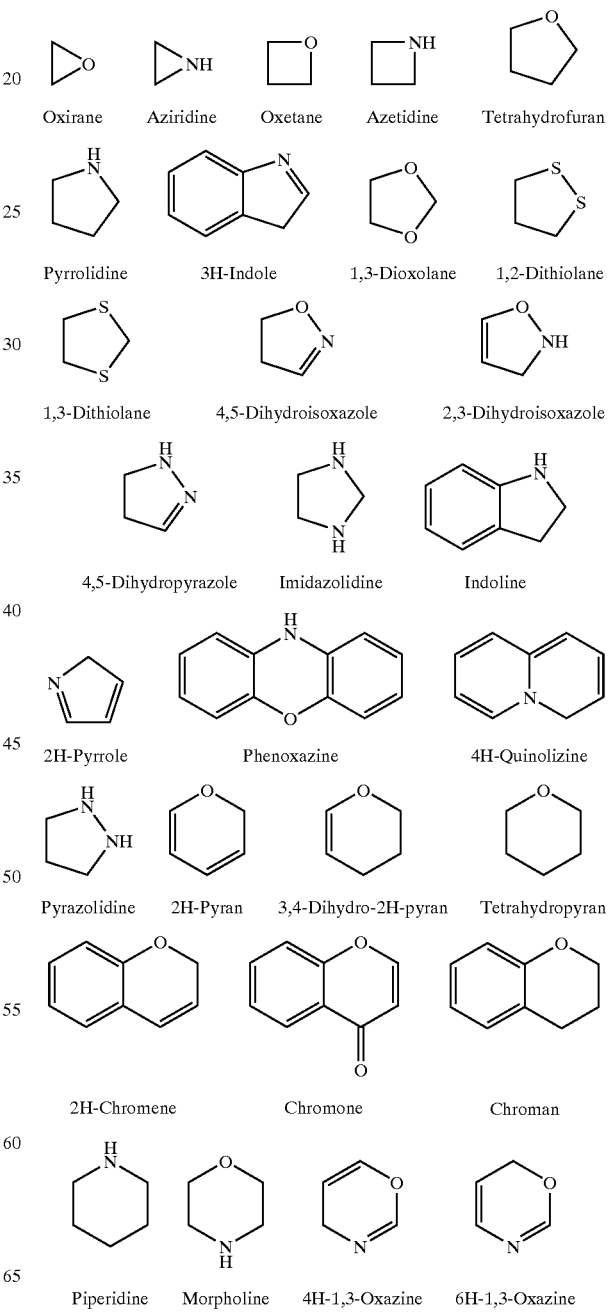

member atoms, in the ring. Bicyclic heterocycloalkyl rings contain from about 7 to about 17 ring atoms, preferably from 7 to 12 ring atoms. Bicyclic heterocycloalkyl rings may be fused, spiro, or bridged ring systems. Preferred bicyclic heterocycloalkyl rings comprise 5-, 6- or 7-membered rings fused to 5-, 6-, or 7-membered rings. Heterocycloalkyl rings may be unsubstituted or substituted with from 1 to 4 substituents on the ring. Heterocycloalkyl may be substituted with halo, cyano, hydroxy, carboxy, keto, thioketo, amino, acylamino, acyl, amido, alkyl, heteroalkyl, haloalkyl, phenyl, alkoxy, aryloxy or any combination thereof. Preferred substituents on heterocycloalkyl include halo and haloalkyl. Preferred heterocycloalkyl rings include, but are not limited to, the following:

"Heteroaryloxy" is an oxygen radical having a heteroaryl substituent (i.e., —O-heteroaryl). Preferred heteroaryloxy groups include (for example) pyridyloxy, furanyloxy, (thiophene)oxy, (oxazole)oxy, (thiazole)oxy, (isoxazole)oxy, pyrmidinyloxy, pyrazinyloxy, and benzothiazolyloxy.

"Heterocycloalkyl" is a saturated or unsaturated ring containing carbon atoms and from 1 to about 4 (preferably 1 to 3) heteroatoms in the ring. Heterocycloalkyl rings are not aromatic. Heterocycloalkyl rings are monocyclic, or are fused, bridged, or Spiro bicyclic ring systems. Monocyclic heterocycloalkyl rings contain from about 3 to about 9 member atoms (carbon and heteroatoms), preferably from 5 to 7 member atoms, in the ring. Bicyclic heterocycloalkyl rings contain from 7 to 17 member atoms, preferably 7 to 12

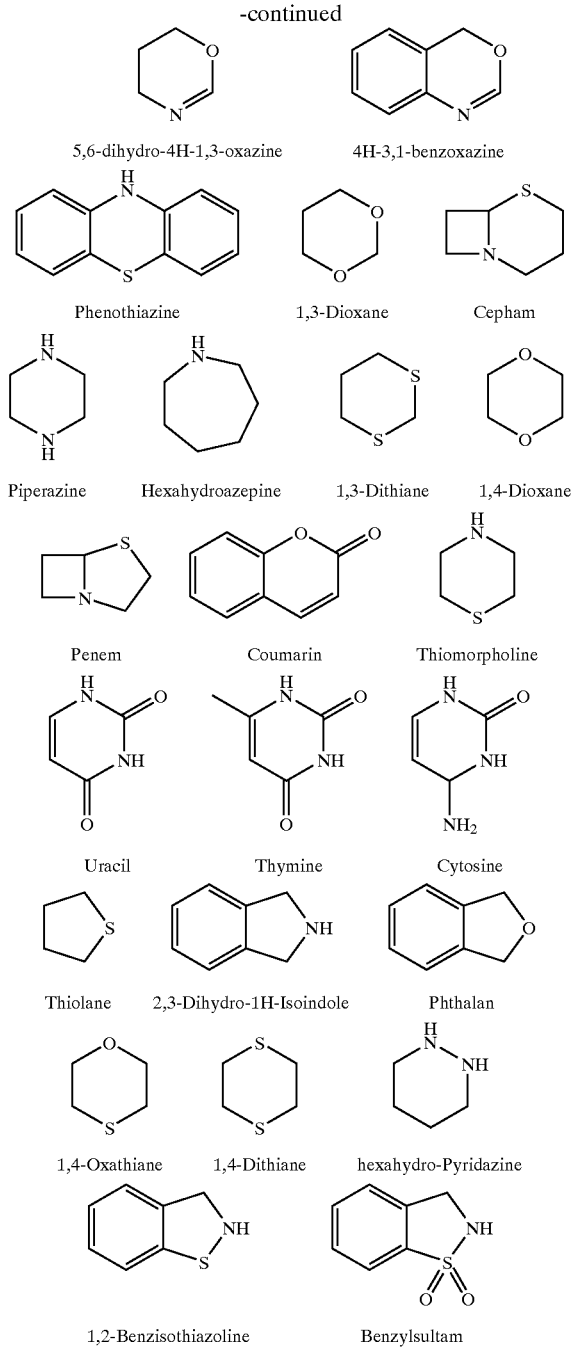

As used herein, "mammalian metalloprotease" refers to the proteases disclosed in the "Background" section of this application. The compounds of the present invention are preferably active against "mammalian metalloproteases", including any metal-containing (preferably zinc-containing) enzyme found in animal, preferably mammalian, sources capable of catalyzing the breakdown of collagen, gelatin or proteoglycan under suitable assay conditions. Appropriate assay conditions can be found, for example, in U.S. Pat. No. 4,743,587, which references the procedure of Cawston, et al., *Anal. Biochem.* (1979) 99:340–345; use of a synthetic substrate is described by Weingarten, H., et al., *Biochem. Biophy. Res. Comm.* (1984) 139:1184–1187. See also Knight, C. G. et al., "A Novel Coumarin-Labelled Peptide for Sensitive Continuous Assays of the Matrix Metalloproteases", *FEBS Letters*, Vol. 296, pp. 263–266 (1992). Any standard method for analyzing the breakdown of these structural proteins can, of course, be used. The present compounds are more preferably active against metalloprotease enzymes that are zinc-containing proteases which are similar in structure to, for example, human stromelysin or skin fibroblast collagenase. The ability of candidate compounds to inhibit metalloprotease activity can, of course, be tested in the assays described above. Isolated metalloprotease enzymes can be used to confirm the inhibiting activity of the invention compounds, or crude extracts which contain the range of enzymes capable of tissue breakdown can be used.

"Spirocycle" is an alkyl or heteroalkyl diradical substituent of alkyl or heteroalkyl wherein said diradical substituent is attached geminally and wherein said diradical substituent forms a ring, said ring containing 4 to 8 member atoms (carbon or heteroatom), preferably 5 or 6 member atoms.

While alkyl, heteroalkyl, cycloalkyl, and heterocycloalkyl groups may be substituted with hydroxy, amino, and amido groups as stated above, the following are not envisioned in the invention:

1. Enols (OH attached to a carbon bearing a double bond).
2. Amino groups attached to a carbon bearing a double bond (except for vinylogous amides).
3. More than one hydroxy, amino, or amido attached to a single carbon (except where two nitrogen atoms are attached to a single carbon atom and all three atoms are member atoms within a heterocycloalkyl ring).
4. Hydroxy, amino, or amido attached to a carbon that also has a heteroatom attached to it.
5. Hydroxy, amino, or amido attached to a carbon that also has a halogen attached to it.

A "pharmaceutically-acceptable salt" is a cationic salt formed at any acidic (e.g., hydroxamic or carboxylic acid) group, or an anionic salt formed at any basic (e.g., amino) group. Many such salts are known in the art, as described in World Patent Publication 87/05297, Johnston et al., published Sep. 11, 1987 incorporated by reference herein. Preferred cationic salts include the alkali metal salts (such as sodium and potassium), and alkaline earth metal salts (such as magnesium and calcium) and organic salts. Preferred anionic salts include the halides (such as chloride salts), sulfonates, carboxylates, phosphates, and the like.

Such salts are well understood by the skilled artisan, and the skilled artisan is able to prepare any number of salts given the knowledge in the art. Furthermore, it is recognized that the skilled artisan may prefer one salt over another for reasons of solubility, stability, formulation ease and the like. Determination and optimization of such salts is within the purview of the skilled artisan's practice.

A "biohydrolyzable amide" is an amide of a hydroxamic acid-containing (i.e., $R^1$ in Formula (I) is —NHOH) metalloprotease inhibitor that does not interfere with the inhibitory activity of the compound, or that is readily converted in vivo by an animal, preferably a mammal, more preferably a human subject, to yield an active metalloprotease inhibitor. Examples of such amide derivatives are alkoxyamides, where the hydroxyl hydrogen of the hydroxamic acid of Formula (I) is replaced by an alkyl moiety, and acyloxyamides, where the hydroxyl hydrogen is replaced by an acyl moiety (i.e., R—C(=O)—).

A "biohydrolyzable hydroxy imide" is an imide of a hydroxamic acid-containing metalloprotease inhibitor that does not interfere with the metalloprotease inhibitory activity of these compounds, or that is readily converted in vivo by an animal, preferably a mammal, more preferably a human subject to yield an active metalloprotease inhibitor. Examples of such imide derivatives are those where the amino hydrogen of the hydroxamic acid of Formula (I) is replaced by an acyl moiety (i.e., R—C(=O)—).

A "biohydrolyzable ester" is an ester of a carboxylic acid-containing (i.e., $R^1$ in Formula (I) is —OH) metalloprotease inhibitor that does not interfere with the metalloprotease inhibitory activity of these compounds or that is readily converted by an animal to yield an active metalloprotease inhibitor. Such esters include lower alkyl esters, lower acyloxy-alkyl esters (such as acetoxymethyl, acetoxyethyl, aminocarbonyloxymethyl, pivaloyloxymethyl and pivaloyloxyethyl esters), lactonyl esters (such as phthalidyl and thiophthalidyl esters), lower alkoxyacyloxyalkyl esters (such as methoxycarbonyloxymethyl, ethoxycarbonyloxyethyl and isopropoxycarbonyloxyethyl esters), alkoxyalkyl esters, choline esters and alkyl acylamino alkyl esters (such as acetamidomethyl esters).

A "solvate" is a complex formed by the combination of a solute (e.g., a metalloprotease inhibitor) and a solvent (e.g., water). See J. Honig et al., *The Van Nostrand Chemist's Dictionary*, p. 650 (1953). Pharmaceutically-acceptable solvents used according to this invention include those that do not interfere with the biological activity of the metalloprotease inhibitor (e.g., water, ethanol, acetic acid, N,N-dimethylformamide and others known or readily determined by the skilled artisan).

The terms "optical isomer", "stereoisomer", and "diastereomer" have the standard art recognized meanings (see, e.g., *Hawley's Condensed Chemical Dictionary*, 11th Ed.). The illustration of specific protected forms and other derivatives of the compounds of the instant invention is not intended to be limiting. The application of other useful protecting groups, salt forms, etc. is within the ability of the skilled artisan.

II. Compounds:

The subject invention involves compounds of Formula (I):

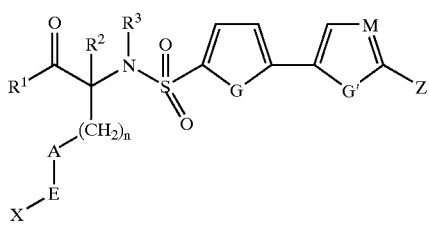

(I)

where $R^1$, $R^2$, $R^3$, n, A, E, X, G, G', M and Z have the meanings described above. The following provides a description of particularly preferred moieties, but is not intended to limit the scope of the claims.

$R^1$ is selected from —OH and —NHOH, preferably —OH.

$R^2$ is selected from hydrogen, alkyl, alkenyl, alkynyl, heteroalkyl, haloalkyl, cycloalkylalkyl, heterocycloalkylalkyl, arylalkyl and heteroarylalkyl; preferably hydrogen or alkyl, more preferably hydrogen.

$R^3$ is selected from alkyl, alkenyl, alkynyl, heteroalkyl, haloalkyl, cycloalkyl, heterocycloalkyl, arylalkyl and heteroarylalkyl; preferably alkyl, heteroalkyl, heterocycloalkylalkyl, arylalkyl or heteroarylalkyl.

n is from 0 to about 4, preferably 0 or 1, more preferably 0.

A is a substituted or unsubstituted, monocyclic heterocycloalkyl having from 3 to 8 ring atoms, of which 1 to 3 are heteroatoms. Preferably, A will contain from 5 to 8 ring atoms, more preferably 6 or 8 ring atoms. A is preferably substituted or unsubstituted piperidine, tetrahydropyran, tetrahydrothiopyran, perhydroazocine; more preferably piperidine, tetrahydropyran or tetrahydrothiopyran. Alternatively, A and $R^2$ can together form a substituted or unsubstituted, monocyclic heterocycloalkyl having from 3 to 8 (preferably 5 to 8, more preferably 6 or 8) ring atoms and 1 to 3 ring heteroatoms. Preferred are those rings as described when A does not combine with R to form a ring.

E is selected from a covalent bond, $C_1$–$C_4$ alkyl, —C(=O)—, —C(=O)O—, C(=O)N($R^4$)—, —$SO_2$—, or —C(=S)N($R^4$)—. In the preferred embodiment E is selected from a bond, $C_1$–$C_3$ alkyl, —C(=O), —C(=O)O—, —C(=O)N($R^4$)—, or —$SO_2$—, more preferably E is $C_1$–$C_2$ alkyl, C(=O)—, —C(=O)O—, or —C(=O)N($R^4$)—.

$R^4$ is selected from hydrogen, alkyl, alkenyl, alkynyl, heteroalkyl, haloalkyl, cycloalkyl, heterocycloalkyl, aryl, arylalkyl, heteroaryl and heteroarylalkyl; preferably hydrogen or lower alkyl.

X is selected from hydrogen, alkyl, alkenyl, alkynyl, heteroalkyl, haloalkyl, aryl, arylalkyl, heteroaryl, heteroarylalkyl, cycloalkyl and heterocycloalkyl. X is preferably hydrogen, alkyl, heteroalkyl, aryl, arylalkyl, heteroaryl, heteroarylalkyl, cycloalkyl or heterocycloalkyl; most preferably alkyl, heteroalkyl, aryl, arylalkyl, heteroaryl or heteroarylalkyl. Alternatively, and preferably, X and $R^4$ join to form a substituted or unsubstituted, monocyclic heterocycloalkyl having from 3 to 8 ring atoms of which 1 to 3 are heteroatoms. When X and $R^4$ form a ring, preferred are 5 to 7 membered rings with 1 or 2 heteroatoms.

G is selected from —S—, —O—, —N($R^5$)—, —C($R^5$)=C($R^{5'}$), —N=C($R^5$)— and —N=N—; in a preferred embodiment, G is —S— or —C($R^5$)=C($R^{5'}$)—. Each $R^5$ and $R^{5'}$ is independently selected from hydrogen, alkyl, alkenyl, alkynyl, heteroalkyl, aryl, heteroaryl, cycloalkyl, and heterocycloalkyl; preferably at least one of $R^5$ and $R^{5'}$ is hydrogen, more preferably both are hydrogen.

G' is selected from —S—, —O—, —N($R^6$)—, —C($R^6$)=C($R^{6'}$)—, —N=C($R^6$)— and —N=N—; in a preferred embodiment, G' is —S— or —C($R^6$)=C($R^{6'}$)—. Each $R^6$ and $R^{6'}$ is independently selected from hydrogen, alkyl, alkenyl, alkynyl, heteroalkyl, aryl, heteroaryl, cycloalkyl, and heterocycloalkyl; preferably at least one of $R^6$ and $R^{6'}$ is hydrogen, more preferably both are hydrogen.

M is selected from —CH— and —N—; preferably M is —CH—.

Z is —($CR^7R^{7'}$)$_a$—L—$R^8$ where a is from 0 to about 4, preferably 0 or 1. Each $R^7$ and $R^{7'}$ is independently selected from hydrogen, alkyl, alkenyl, alkynyl, aryl, heteroalkyl, heteroaryl, cycloalkyl, heterocycloalkyl, halogen, haloalkyl, hydroxy and alkoxy; preferably each $R^7$ is hydrogen and each $R^{7'}$ is independently hydrogen or lower alkyl.

L is nil or a connecting group selected from a covalent bond, —O—, —$SO_b$—, —C(=O)—, —C(=O)N($R^9$)—, —N($R^9$)—, and —N($R^9$)C(=O)—; preferably L is —O—, —S—, —$SO_2$—, —C(=O)N($R^9$)—, —N($R^9$)—, and —N($R^9$)C(=O)—; more preferably L is —O— or —S—. b is from 0 to 2. $R^9$ is selected from hydrogen, alkyl. alkenyl, alkynyl, aryl, heteroaryl, heteroalkyl, heteroaryl, cycloalkyl. heterocycloalkyl, and haloalkyl; $R^9$ is preferably hydrogen, lower alkyl or aryl. Alternatively, $R^7$ and $R^9$, together with the atoms to which they are bonded, join to form an optionally substituted heterocyclic ring containing from 5 to 8 (preferably 5 or 6) atoms of which 1 to 3 (preferably 1 or 2) are heteroatoms.

$R^8$ is selected from hydrogen, alkyl, alkenyl, alkynyl, halogen, heteroalkyl, haloalkyl, aryl, heteroaryl, cycloalkyl, and heterocycloalkyl; preferably $R^8$ is halogen, lower alkyl, lower heteroalkyl or aryl. Alternatively, $R^8$ and $R^9$, together with the atoms to which they are bonded, join to form an optionally substituted heterocyclic ring containing from 5 to 8 (preferably 5 or 6) atoms of which 1 to 3 (preferably 1 or 2) are heteroatoms.

III. Compound Preparation:

The compounds of the invention can be prepared using a variety of procedures. The starting materials used in preparing the compounds of the invention are known, made by known methods, or are commercially available. Particularly preferred syntheses are described in the following general reaction schemes. (The R groups used to illustrate the reaction schemes do not necessarily correlate to the respective R groups used to describe the various aspects of the Formula I compounds. That is, for example, $R^1$ in Formula (I) does not represent the same moiety as $R^1$ here). Specific examples for making the compounds of the present invention are set forth in Section VII, below.

In Scheme 1, the ketone S1a is a commercially available material. Upon reaction with phosphonate S1b it can be converted to unsaturated ester S1c in a very good yield. Hydrogenolysis of this material under standard conditions provides aminoester S1d. At this stage substituents $R^1$ and $R^2$ can be introduced using reductive amination followed by sulfonylation or, in reverse, sulfonylation followed by alkylation of the sulfonamide group.

The Boc protective group of sulfonamide S1e can be removed under conditions well established in the art providing aminoester S1f. The methyl ester group of this compound can be hydrolyzed under standard conditions to produce amino-acid S1g. At this stage the $R^3$ substituent of the piperazine nitrogen atom can be introduced under variety of conditions. Thus, reactions of reductive amination, acylation, arylation, carbamoylation, sulfonylation and urea formation all result in good yields of the target carboxylic acid S1i.

Alternatively, substituent $R^3$ can, under standard conditions, be introduced at the stage of methyl ester S1f to produce a fully functionalized compound S1h. Standard hydrolysis of the ester functionality of S1h leads to the target carboxylic acid S1i.

Scheme 1

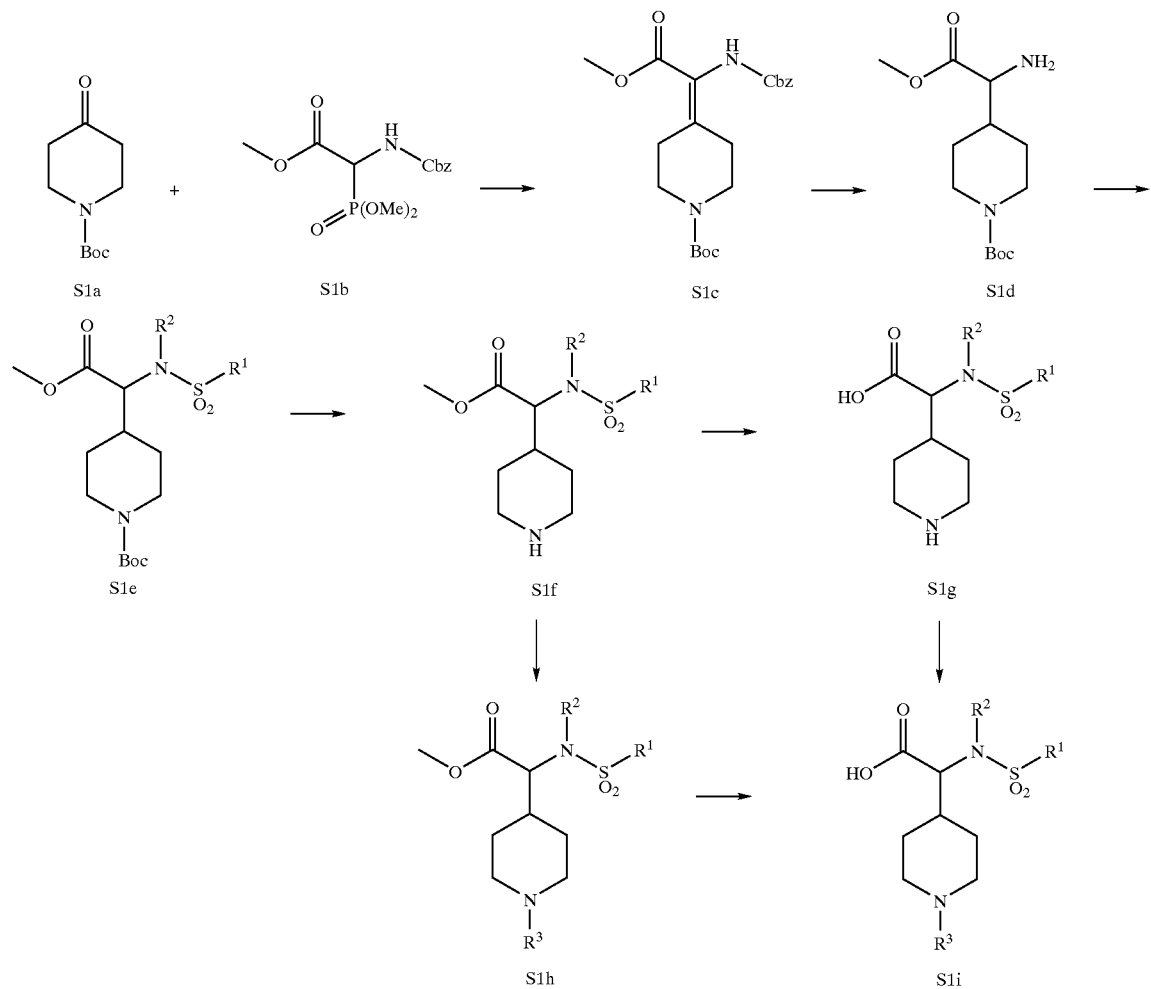

Scheme 2

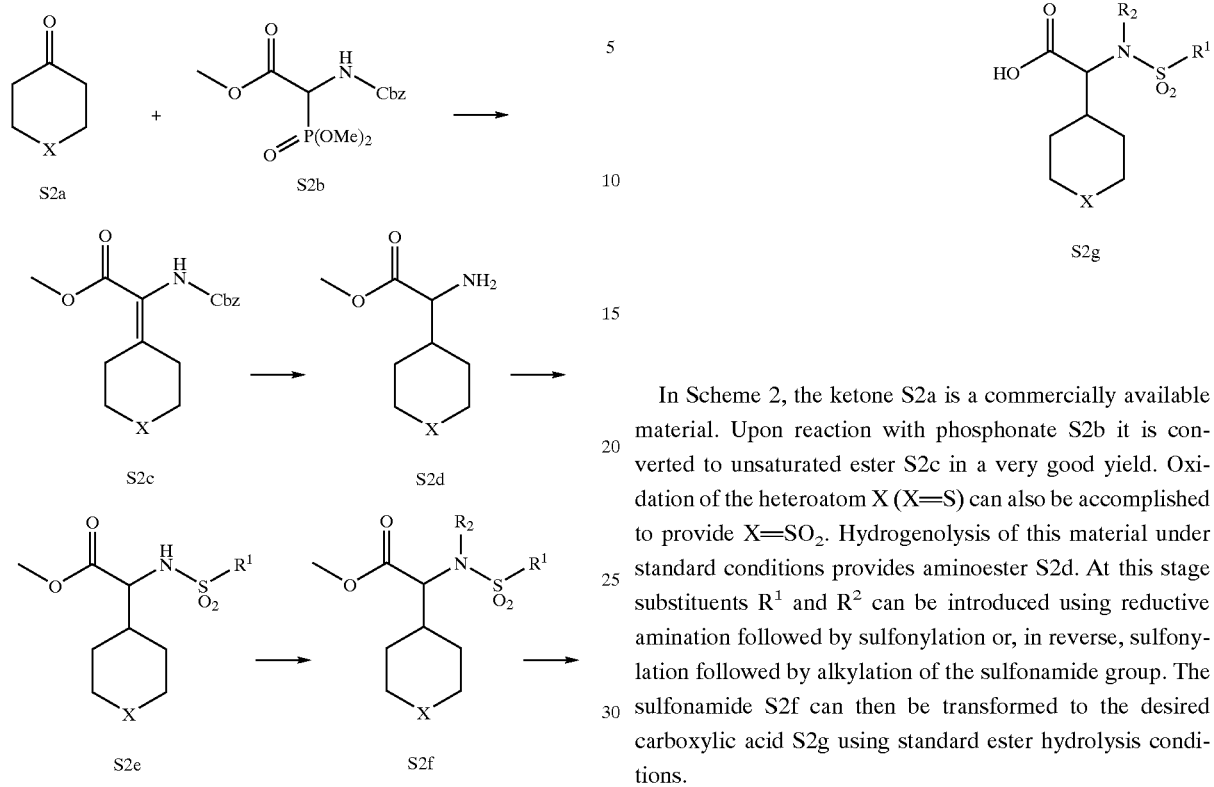

In Scheme 2, the ketone S2a is a commercially available material. Upon reaction with phosphonate S2b it is converted to unsaturated ester S2c in a very good yield. Oxidation of the heteroatom X (X=S) can also be accomplished to provide X=SO$_2$. Hydrogenolysis of this material under standard conditions provides aminoester S2d. At this stage substituents R$^1$ and R$^2$ can be introduced using reductive amination followed by sulfonylation or, in reverse, sulfonylation followed by alkylation of the sulfonamide group. The sulfonamide S2f can then be transformed to the desired carboxylic acid S2g using standard ester hydrolysis conditions.

Scheme 3

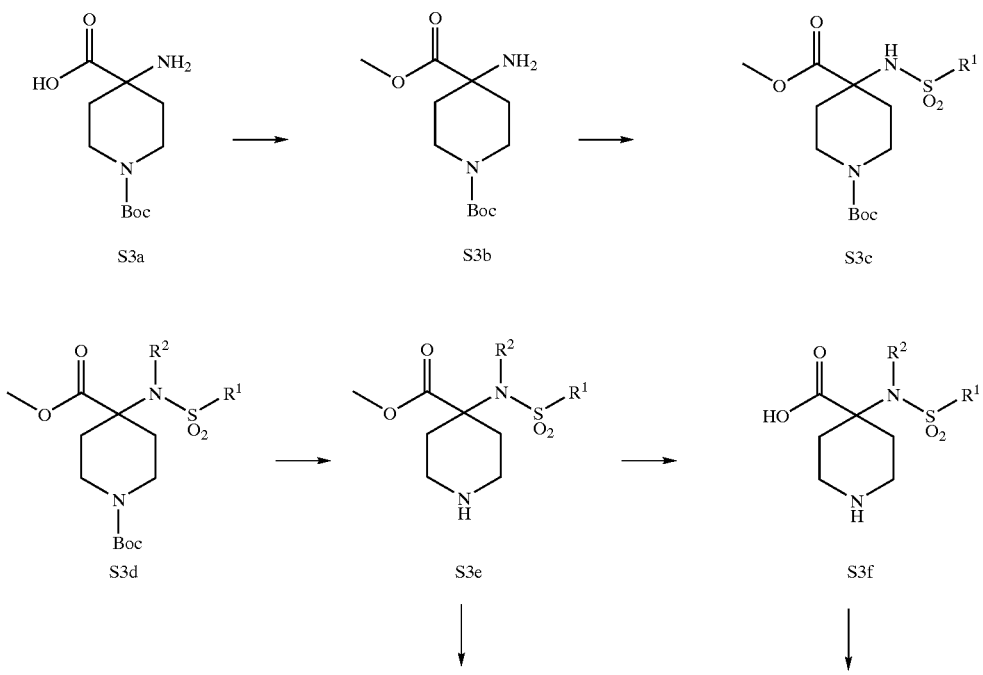

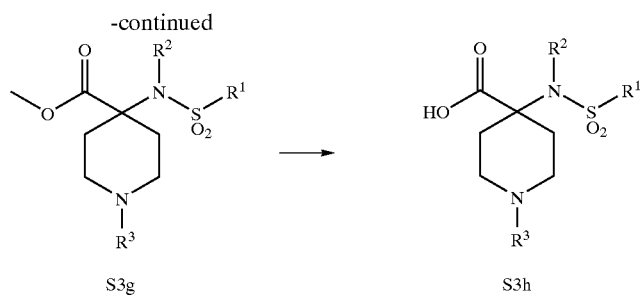

S3g → S3h

In Scheme 3, the amino acid S3a is a commercially available material. Standard conditions can be used to convert S3a to the corresponding methyl ester S3b. At this stage substituent $R^1$ is introduced in the sulfonylation reaction to arrive at convenient intermediate S3c. If necessary, a more elaborate $R^1$ substituent is introduced in the sequence of several synthetic steps. Substituent $R^2$ can then be introduced via standard alkylation conditions to produce intermediate S3d.

The Boc protective group of sulfonamide S3d can be removed under conditions well established in the art providing aminoester S3e. The ester group of this compound can be hydrolyzed under standard conditions to produce amino-acid S3f. At this stage the $R^3$ substituent of the piperazine nitrogen atom can be introduced under a variety of conditions. Thus, reactions of reductive amination, acylation, arylation, carbamoylation, sulfonylation and urea formation all result in good yields of the target carboxylic acid ester S3g. Standard hydrolysis of the ester functionality of S3g leads to the target carboxylic acid S3h.

The methyl ester S3g serves as a convenient intermediate in the synthesis of hydroxamic acid S3h. Thus treatment of S3g with a basic solution of hydroxylamine in methanol provides the corresponding hydroxamic acid in a single step. Alternatively, the carboxylic S3h can be transformed to the hydroxamic acid through the two step transformation involving 1) coupling with an O-protected form of hydroxylamine, and 2) removal of the protective group. Protective groups well known in the art (e.g. benzyl, tert-butyl, tert-butyldimethylsilyl) can be used for this transformation.

These steps may be varied to increase yield of desired product. The skilled artisan will recognize the judicious choice of reactants, solvents, and temperatures is an important component in any successful synthesis. Determination of optimal conditions, etc. is routine. Thus the skilled artisan can make a variety of compounds using the guidance of the schemes above.

It is recognized that the skilled artisan in the art of organic chemistry can readily carry out standard manipulations of organic compounds without further direction; that is, it is well within the scope and practice of the skilled artisan to carry out such manipulations. These include, but are not limited to, reduction of carbonyl compounds to their corresponding alcohols, oxidations of hydroxyls and the like, acylations, aromatic substitutions, both electrophilic and nucleophilic, etherifications, esterification and saponification and the like. Examples of these manipulations are discussed in standard texts such as March, *Advanced Organic Chemistry* (Wiley), Carey and Sundberg, *Advanced Organic Chemistry* (Vol. 2) and other art that the skilled artisan is aware of.

The skilled artisan will also readily appreciate that certain reactions are best carried out when another potentially reactive functionality on the molecule is masked or protected, thus avoiding any undesirable side reactions and/or increasing the yield of the reaction. Often the skilled artisan utilizes protecting groups to accomplish such increased yields or to avoid the undesired reactions. These reactions are found in the literature and are also well within the scope of the skilled artisan. Examples of many of these manipulations can be found for example in T. Greene, *Protecting Groups in Organic Synthesis*. Of course, amino acids used as starting materials with reactive side chains are preferably blocked to prevent undesired side reactions.

The compounds of the invention may have one or more chiral centers. As a result, one may selectively prepare one optical isomer, including diastereomer and enantiomer, over another, for example by chiral starting materials, catalysts or solvents, or may prepare both stereoisomers or both optical isomers, including diastereomers and enantiomers at once (a racemic mixture). Since the compounds of the invention may exist as racemic mixtures, mixtures of optical isomers, including diastereomers and enantiomers, or stereoisomers may be separated using known methods, such as chiral salts, chiral chromatography and the like.

In addition, it is recognized that one optical isomer, including diastereomer and enantiomer, or stereoisomer may have favorable properties over the other. Thus when disclosing and claiming the invention, when one racemic mixture is disclosed, it is clearly contemplated that both optical isomers, including diastereomers and enantiomers, or stereoisomers substantially free of the other are disclosed and claimed as well.

IV. Methods of Use:

Metalloproteases (MPs) found in the body operate, in part, by breaking down the extracellular matrix, which comprises extracellular proteins and glycoproteins. Inhibitors of metalloproteases are useful in treating diseases caused, at least in part, by the breakdown of such proteins and glycoproteins. These proteins and glycoproteins play an important role in maintaining the size, shape, structure and stability of tissue in the body. Thus, MPs are intimately involved in tissue remodeling.

As a result of this activity, MPs have been said to be active in many disorders involving either the: (1) breakdown of tissues including opthalmic diseases; degenerative diseases, such as arthritis, multiple sclerosis and the like; and metastasis or mobility of tissues in the body; or (2) remodeling of tissues including cardiac disease, fibrotic disease, scarring, benign hyperplasia, and the like.

The compounds of the present invention prevent or treat disorders, diseases and/or unwanted conditions which are characterized by unwanted or elevated activity by MPs. For example, the compounds can be used to inhibit MPs which:

1. destroy structural proteins (i.e. the proteins that maintain tissue stability and structure);
2. interfere in inter/intracellular signaling, including those implicated in cytokine up-regulation, and/or cytokine processing and/or inflammation, tissue degradation and other maladies [Mohler K M, et al, Nature 370 (1994) 218–220, Gearing A J H, et al, Nature 370 (1994) 555–557 McGeehan G M, et al, Nature 370 (1994) 558–561]; and 3. facilitate processes which are undesired in the subject being treated, for example, the processes of sperm maturation, egg fertilization and the like. The term "treatment" is used herein to mean that, at a minimum, administration of a compound of the present invention that mitigates a "MP related disorder or disease" in a mammalian subject, preferably in humans. Thus, the term "treatment" includes: preventing an MP related disorder from occurring in a mammal, particularly when the mammal is predisposed to acquiring the MP related disorder, but has not yet been diagnosed with the disease; inhibiting the MP related disorder; and/or alleviating or reversing the mP related disorder. Insofar as the methods of the present invention are directed to preventing an MP related disorder, it is understood that the term "prevent" does not require that the MP related disorder be completely thwarted. (See Webster's Ninth Collegiate Dictionary.) Rather, as used herein, the term "preventing" refers to the ability of the skilled artisan to identify a population that is susceptible to MP related disorder, such that administration of the compounds of the present invention may occur prior to the onset of the symptoms of the MP related disorder. The population that is at risk of a MP related disorder, for example as heart disease, are those who have a genetic predisposition to heart disease as indicated by family history of the disease. Other risk factors include obesity, stress, and/or a diet high in atherogenic lipids.

Thus, the patient population is identifiable and could receive the adminstration of a composition of the present invention before progression of the disease. Thus, progression of the MP related disorder in such individuals would be "prevented".

As used herein, an "MP related disorder" or "MP related disease" is one that involves unwanted or elevated MP activity in the biological manifestation of the disease or disorder; in the biological cascade leading to the disorder; or as a symptom of the disorder. This "involvement" of the MP includes:

1. The unwanted or elevated MP activity as a "cause" of the disorder or biological manifestation, whether the activity is elevated genetically, by infection, by autoimmunity, trauma, biomechanical causes, lifestyle [e.g. obesity] or by some other cause;

2. The MP as part of the observable manifestation of the disease or disorder. That is, the disease or disorder is measurable in terms of the increased MP activity. From a clinical standpoint, unwanted or elevated MP levels indicate the disease, however, MPs need not be the "hallmark" of the disease or disorder; or 3. The unwanted or elevated MP activity is part of the biochemical or cellular cascade that results or relates to the disease or disorder. In this respect, inhibition of the MP activity interrupts the cascade, and thus controls the disease.

The term "treatment" is used herein to mean that, at a minimum, administration of a compound of the present invention mitigates a disease associated with unwanted or elevated MP activity in a mammalian subject, preferably in humans. Thus, the term "treatment" includes: preventing an MP-mediated disease from occurring in a mammal, particularly when the mammal is predisposed to acquiring the disease, but has not yet been diagnosed with the disease; inhibiting the MP-mediated disease; and/or alleviating or reversing the MP-mediated disease. Insofar as the methods of the present invention are directed to preventing disease states associated with unwanted MP activity, it is understood that the term "prevent" does not require that the disease state be completely thwarted. (See Webster's Ninth Collegiate Dictionary.) Rather, as used herein, the term preventing refers to the ability of the skilled artisan to identify a population that is susceptible to MP-related disorders, such that administration of the compounds of the present invention may occur prior to onset of the disease. The term does not imply that the disease state be completely avoided. For example, osteoarthritis (OA) is the most common rhueumatological disease with some joint changes radiologically detectable in 80% of people over 55 years of age. Fife, R. S., "A Short History of Osteoarthritis", Osteoarthritis: Diagnosis and Medical/Surgical Management, R. W. Moskowitz, D. S. Howell, V. M. Goldberg and H. J. Mankin Eds., p 11–14 (1992). A common risk factor that increases the incidence of OA is traumatic injury of the joint. Surgical removal of the meniscus following knee injury increases the risk of radiographically detectable OA and this risk increases with time. Roos, H et al. "Knee Osteoarthritis After Menisectomy: Prevalence of Radiographic Changes After Twenty-one Years, Compared with Matched Controls." Arthritis Rheum., Vol. 41, pp 687–693; Roos, H et al. "Osteoarthritis of the Knee After Injury to the Anterior Cruciate Ligament or Meniscus: The Influence of Time and Age." Osteoarthritis Cartilege., Vol. 3, pp 261–267 (1995). Thus, this patient population is identifiable and could receive administration of a compound of the present invention before progression of the disease. Thus, progression of OA in such individuals would be "prevented".

Advantageously, many MPs are not distributed evenly throughout the body. Thus, the distribution of MPs expressed in various tissues are often specific to those tissues. For example, the distribution of metalloproteases implicated in the breakdown of tissues in the joints is not the same as the distribution of metalloproteases found in other tissues. Though not essential for activity or efficacy, certain diseases, disorders, and unwanted conditions preferably are treated with compounds that act on specific MPs found in the affected tissues or regions of the body. For example, a compound which displays a higher degree of affinity and inhibition for an MP found in the joints (e.g. chondrocytes) would be preferred for treatment of a disease, disorder, or unwanted condition found there than other compounds which are less specific.

In addition, certain inhibitors are more bioavailable to certain tissues than others. Choosing an MP inhibitor which is more bioavailable to a certain tissue and which acts on the specific MPs found in that tissue, provides for specific treatment of the disease, disorder, or unwanted condition. For example, compounds of this invention vary in their ability to penetrate into the central nervous system. Thus, compounds may be selected to produce effects mediated through MPs found specifically outside the central nervous system.

Determination of the specificity of an inhibitor of a specific MP is within the skill of the artisan in that field. Appropriate assay conditions can be found in the literature. Specifically, assays are known for stromelysin and collagenase. For example, U.S. Pat. No. 4,743,587 references the procedure of Cawston, et al., *Anal Biochem* (1979) 99:340–345. See also, Knight, C. G. et al., "A Novel Coumarin-Labelled Peptide for Sensitive Continuous Assays of the Matrix Metalloproteases", *FEBS Letters*, Vol. 296, pp. 263–266 (1992). The use of a synthetic substrate in an assay is described by Weingarten, H., et al., *Biochem Biophy Res Comm* (1984) 139:1184–1187. Any standard method for analyzing the breakdown of structural proteins by MPs can, of course, be used. The ability of compounds of the invention to inhibit metalloprotease activity can, of course, be tested in the assays found in the literature, or variations thereof. Isolated metalloprotease enzymes can be used to confirm the inhibiting activity of the invention compounds, or crude extracts which contain the range of enzymes capable of tissue breakdown can be used.

The compounds of this invention are also useful for prophylactic or acute treatment. They are administered in any way the skilled artisan in the fields of medicine or pharmacology would desire. It is immediately apparent to the skilled artisan that preferred routes of administration will depend upon the disease state being treated and the dosage form chosen. Preferred routes for systemic administration include administration perorally or parenterally.

However, the skilled artisan will readily appreciate the advantage of administering the MP inhibitor directly to the affected area for many diseases, disorders, or unwanted conditions. For example, it may be advantageous to administer MP inhibitors directly to the area of the disease, disorder, or unwanted condition such as in the area affected by surgical trauma (e.g., angioplasty), scarring, burning (e.g., topical to the skin), or for opthalmic and periodontal indications.

Because the remodeling of bone involves MPs, the compounds of the invention are useful in preventing prosthesis loosening. It is known in the art that over time prostheses loosen, become painful, and may result in further bone injury, thus demanding replacement. The need for replacement of such prostheses includes those such as in, joint replacements (for example hip, knee and shoulder replacements), dental prosthesis, including dentures, bridges and prosthesis secured to the maxilla and/or mandible.

MPs are also active in remodeling of the cardiovascular system (for example, in congestive heart failure). It has been suggested that one of the reasons angioplasty has a higher than expected long term failure rate (reclosure over time) is that MP activity is not desired or is elevated in response to what may be recognized by the body as "injury" to the basement membrane of the vessel. Thus regulation of MP activity in indications such as dilated cardiomyopathy, congestive heart failure, atherosclerosis, plaque rupture, reperfusion injury, ischemia, chronic obstructive pulmonary disease, angioplasty restenosis and aortic aneurysm may increase long term success of any other treatment, or may be a treatment in itself.

In one aspect of the present invention, the compounds of Formula I of the present invention may be effective in preventing or treating myocardial infaction (herinafter "MI"). MI, also known as a "heart attack" or "heart failure", is a condition caused by partial or complete occlusion of one or more of the coronary arteries, usually due to rupture of an atherosclerotic plaque. The occlusion of the coronary artery results in cardiac ischemia. MMPs are implicated in artherosclerotic plaque rupture. MMPs are implicated in artherosclerotic plaque rupture. See e.g., Galis, Z. S., et al., J. Clin. Invest. 1994;94:2493–503; Lee, R. T., et al., Arterioscler. Thromb. Vasc. Biol. 1996;16:1070–73; Schonbeck, U. et al., Circulation Research 1997; 81(3), 448–454. Libby, P. et al., Circ. 1995;91:2844–50.

In another aspect of the invention, the compounds of the present invention may be effective in preventing or treating progressive ventricular dilation after a MI, the major contributing factor to the development of post-MI chronic heart failure (hereinafter "CHF"). Thus, in yet still another aspect of the invention, the compounds of the present invention may be effective in preventing or treating the development of post-MI chronic heart failure.

In skin care, MPs are implicated in the remodeling or "turnover" of skin. As a result, the regulation of MPs improves treatment of skin conditions including but not limited to, wrinkle repair, regulation and prevention and repair of ultraviolet induced skin damage. Such a treatment includes prophylactic treatment or treatment before the physiological manifestations are obvious. For example, the MP may be applied as a pre-exposure treatment to prevent ultaviolet damage and/or during or after exposure to prevent or minimize post-exposure damage. In addition, MPs are implicated in skin disorders and diseases related to abnormal tissues that result from abnormal turnover, which includes metalloprotease activity, such as epidermolysis bullosa, psoriasis, scleroderma and atopic dermatitis. The compounds of the invention are also useful for treating the consequences of "normal" injury to the skin including scarring or "contraction" of tissue, for example, following burns. MP inhibition is also useful in surgical procedures involving the skin for prevention of scarring, and promotion of normal tissue growth including in such applications as limb reattachment and refractory surgery (whether by laser or incision).

In addition, MPs are related to disorders involving irregular remodeling of other tissues, such as bone, for example, in otosclerosis and/or osteoporosis, or for specific organs, such as in liver cirrhosis and fibrotic lung disease. Similarly in diseases such as multiple sclerosis, MPs may be involved in the irregular modeling of blood brain barrier and/or myelin sheaths of nervous tissue. Thus regulating MP activity may be used as a strategy in treating, preventing, and controlling such diseases.

MPs are also thought to be involved in many infections, including cytomegalovirus [CMV]; retinitis; HIV, and the resulting syndrome, AIDS.

MPs may also be involved in extra vascularization where surrounding tissue needs to be broken down to allow new blood vessels such as in angiofibroma and hemangioma.

Since MPs break down the extracellular matrix, it is contemplated that inhibitors of these enzymes can be used as birth control agents, for example in preventing ovulation, in preventing penetration of the sperm into and through the extracellular milieu of the ovum, implantation of the fertilized ovum and in preventing sperm maturation.

In addition they are also contemplated to be useful in preventing or stopping premature labor and delivery.

Since MPs are implicated in the inflammatory response and in the processing of cytokines, the compounds are also useful as anti-inflammatories, for use in disease where inflammation is prevalent including, inflammatory bowel disease, Crohn's disease, ulcerative colitis, pancreatitis, diverticulitis, asthma or related lung disease, rheumatoid arthritis, gout and Reiter's Syndrome.

Where autoimmunity is the cause of the disorder, the immune response often triggers MP and cytokine activity. Regulation of MPs in treating such autoimmune disorders is a useful treatment strategy. Thus MP inhibitors can be used for treating disorders including, lupus erythmatosis, ankylosing spondylitis, and autoimmune keratitis. Sometimes the side effects of autoimmune therapy result in exacerbation of other conditions mediated by MPs, here MP inhibitor therapy is effective as well, for example, in autoimmune-therapy-induced fibrosis.

In addition, other fibrotic diseases lend themselves to this type of therapy, including pulmonary disease, bronchitis, emphysema, cystic fibrosis, acute respiratory distress syndrome (especially the acute phase response).

Where MPs are implicated in the undesired breakdown of tissue by exogenous agents, these can be treated with MP inhibitors. For example, they are effective as rattle snake bite antidote, as anti-vessicants, in treating allergic inflammation, septicemia and shock. In addition, they are useful as antiparasitics (e.g., in malaria) and antiinfectives. For example, they are thought to be useful in treating or preventing viral infection, including infection which would result in herpes, "cold" (e.g., rhinoviral infection), meningitis, hepatitis, HIV infection and AIDS.

MP inhibitors are also thought to be useful in treating Alzheimer's disease, amyotrophic lateral sclerosis (ALS), muscular dystrophy, complications resulting from or arising out of diabetes, especially those involving loss of tissue viability, coagulation, Graft vs. Host disease, leukemia, cachexia, anorexia, proteinuria, and perhaps regulation of hair growth.

For some diseases, conditions or disorders MP inhibition is contemplated to be a preferred method of treatment. Such diseases, conditions or disorders include, arthritis (including osteoarthritis and rheumatoid arthritis), cancer (especially the prevention or arrest of tumor growth and metastasis), ocular disorders (especially corneal ulceration, lack of corneal healing, macular degeneration, and pterygium), and gum disease (especially periodontal disease, and gingivitis)

Compounds preferred for, but not limited to, the treatment of arthritis (including osteoarthritis and rheumatoid arthritis) are those compounds that are selective for the matrix metalloproteases and the disintegrin metalloproteases.

Compounds preferred for, but not limited to, the treatment of cancer (especially the prevention or arrest of tumor growth and metastasis) are those compounds that preferentially inhibit gelatinases or type IV collagenases.

Compounds preferred for, but not limited to, the treatment of ocular disorders (especially corneal ulceration, lack of corneal healing, macular degeneration, and pterygium) are those compounds that broadly inhibit metalloproteases. Preferably these compounds are administered topically, more preferably as a drop or gel.

Compounds preferred for, but not limited to, the treatment of gum disease (especially periodontal disease, and gingivitis) are those compounds that preferentially inhibit collagenases.

V. Compositions:

The compositions of the invention comprise:

(a) a safe and effective amount of a compound of the invention; and (b) a pharmaceutically-acceptable carrier.

As discussed above, numerous diseases are known to be mediated by excess or undesired metalloprotease activity. These include tumor metastasis, osteoarthritis, rheumatoid arthritis, skin inflammation, ulcerations, particularly of the cornea, reaction to infection, periodontitis and the like. Thus, the compounds of the invention are useful in therapy with regard to conditions involving this unwanted activity.

The invention compounds can therefore be formulated into pharmaceutical compositions for use in treatment or prophylaxis of these conditions. Standard pharmaceutical formulation techniques are used, such as those disclosed in *Remington's Pharmaceutical Sciences*, Mack Publishing Company, Easton, Pa., latest edition.

A "safe and effective amount" of a Formula (I) compound is an amount that is effective, to inhibit metalloproteases at the site(s) of activity, in an animal, preferably a mammal, more preferably a human subject, without undue adverse side effects (such as toxicity, irritation, or allergic response), commensurate with a reasonable benefit/risk ratio when used in the manner of this invention. The specific "safe and effective amount" will, obviously, vary with such factors as the particular condition being treated, the physical condition of the patient, the duration of treatment, the nature of concurrent therapy (if any), the specific dosage form to be used, the carrier employed, the solubility of the Formula (I) compound therein, and the dosage regimen desired for the composition.

In addition to the subject compound, the compositions of the subject invention contain a pharmaceutically-acceptable carrier. The term "pharmaceutically-acceptable carrier", as used herein, means one or more compatible solid or liquid filler diluents or encapsulating substances which are suitable for administration to an animal, preferably a mammal, more preferably a human. The term "compatible", as used herein, means that the components of the composition are capable of being commingled with the subject compound, and with each other, in a manner such that there is no interaction which would substantially reduce the pharmaceutical efficacy of the composition under ordinary use situations. Pharmaceutically-acceptable carriers must, of course, be of sufficiently high purity and sufficiently low toxicity to render them suitable for administration to the animal, preferably a mammal, more preferably a human being treated.

Some examples of substances which can serve as pharmaceutically-acceptable carriers or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of theobroma; polyols such as propylene glycol, glycerine, sorbitol, mannitol, and polyethylene glycol; alginic acid; emulsifiers, such as the Tweens®; wetting agents, such sodium lauryl sulfate; coloring agents; flavoring agents; tableting agents, stabilizers; antioxidants; preservatives; pyrogen-free water; isotonic saline; and phosphate buffer solutions.

The choice of a pharmaceutically-acceptable carrier to be used in conjunction with the subject compound is basically determined by the way the compound is to be administered.

If the subject compound is to be injected, the preferred pharmaceutically-acceptable carrier is sterile, physiological saline, with blood-compatible suspending agent, the pH of which has been adjusted to about 7.4.

In particular, pharmaceutically-acceptable carriers for systemic administration include sugars, starches, cellulose and its derivatives, malt, gelatin, talc, calcium sulfate, vegetable oils, synthetic oils, polyols, alginic acid, phosphate buffer solutions, emulsifiers, isotonic saline, and pyrogen-free water. Preferred carriers for parenteral administration include propylene glycol, ethyl oleate, pyrrolidone, ethanol, and sesame oil. Preferably, the pharmaceutically-acceptable carrier, in compositions for parenteral administration, comprises at least about 90% by weight of the total composition.

The compositions of this invention are preferably provided in unit dosage form. As used herein, a "unit dosage form" is a composition of this invention containing an amount of a Formula (I) compound that is suitable for administration to an animal, preferably a mammal, more preferably a human subject, in a single dose, according to good medical practice. These compositions preferably contain from about 5 mg (milligrams) to about 1000 mg, more preferably from about 10 mg to about 500 mg, more preferably from about 10 mg to about 300 mg, of a Formula (I) compound.

The compositions of this invention may be in any of a variety of forms, suitable (for example) for oral, rectal, topical, nasal, ocular or parenteral administration. Depending upon the particular route of administration desired, a variety of pharmaceutically-acceptable carriers well-known in the art may be used. These include solid or liquid fillers, diluents, hydrotropes, surface-active agents, and encapsulating substances. Optional pharmaceutically-active materials may be included, which do not substantially interfere with the inhibitory activity of the Formula (I) compound. The amount of carrier employed in conjunction with the Formula (I) compound is sufficient to provide a practical quantity of material for administration per unit dose of the Formula (I) compound. Techniques and compositions for making dosage forms useful in the methods of this invention are described in the following references, all incorporated by reference herein: *Modern Pharmaceutics*, Chapters 9 and 10 (Banker & Rhodes, editors, 1979); Lieberman et al., *Pharmaceutical Dosage Forms: Tablets* (1981); and Ansel, *Introduction to Pharmaceutical Dosage Forms* 2d Edition (1976).

Various oral dosage forms can be used, including such solid forms as tablets, capsules, granules and bulk powders. These oral forms comprise a safe and effective amount, usually at least about 5%, and preferably from about 25% to about 50%, of the Formula (I) compound. Tablets can be compressed, tablet triturates, enteric-coated, sugar-coated, film-coated, or multiple-compressed, containing suitable binders, lubricants, diluents, disintegrating agents, coloring agents, flavoring agents, flow-inducing agents, and melting agents. Liquid oral dosage forms include aqueous solutions, emulsions, suspensions, solutions and/or suspensions reconstituted from non-effervescent granules, and effervescent preparations reconstituted from effervescent granules, containing suitable solvents, preservatives, emulsifying agents, suspending agents, diluents, sweeteners, melting agents, coloring agents and flavoring agents.

The pharmaceutically-acceptable carrier suitable for the preparation of unit dosage forms for peroral administration are well-known in the art. Tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. The selection of carrier components depends on secondary considerations like taste, cost, and shelf stability, which are not critical for the purposes of the subject invention, and can be readily made by a person skilled in the art.

Peroral compositions also include liquid solutions, emulsions, suspensions, and the like. The pharmaceutically-acceptable carriers suitable for preparation of such compositions are well known in the art. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, Avicel" RC-591, tragacanth and sodium alginate; typical wetting agents include lecithin and polysorbate 80; and typical preservatives include methyl paraben and sodium benzoate. Peroral liquid compositions may also contain one or more components such as sweeteners, flavoring agents and colorants disclosed above.

Such compositions may also be coated by conventional methods, typically with pH or time-dependent coatings, such that the subject compound is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methyl cellulose phthalate, ethyl cellulose, Eudragit" coatings, waxes and shellac.

Compositions of the subject invention may optionally include other drug actives.

Other compositions useful for attaining systemic delivery of the subject compounds include sublingual, buccal and nasal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

The compositions of this invention can also be administered topically to a subject, e.g., by the direct laying on or spreading of the composition on the epidermal or epithelial tissue of the subject, or transdermally via a "patch". Such compositions include, for example, lotions, creams, solutions, gels and solids. These topical compositions preferably comprise a safe and effective amount, usually at least about 0.1%, and preferably from about 1% to about 5%, of the Formula (I) compound. Suitable carriers for topical administration preferably remain in place on the skin as a continuous film, and resist being removed by perspiration or immersion in water. Generally, the carrier is organic in nature and capable of having dispersed or dissolved therein the Formula (I) compound. The carrier may include pharmaceutically-acceptable emollients, emulsifiers, thickening agents, solvents and the like.

VI. Methods of Administration:

This invention also provides methods of treating or preventing disorders associated with excess or undesired metalloprotease activity in a human or other animal subject, by administering a safe and effective amount of a Formula (I) compound to said subject. As used herein, a "disorder associated with excess or undesired metalloprotease activity" is any disorder characterized by degradation of matrix proteins. The methods of the invention are useful in treating or preventing disorders described above.

Compositions of this invention can be administered topically or systemically. Systemic application includes any method of introducing Formula (I) compound into the tissues of the body, e.g., intra-articular (especially in treatment of rheumatoid arthritis), intrathecal, epidural, intramuscular, transdermal, intravenous, intraperitoneal, subcutaneous, sublingual, rectal, and oral administration. The Formula (I) compounds of the present invention are preferably administered orally.

The specific dosage of inhibitor to be administered, as well as the duration of treatment, and whether the treatment is topical or systemic are interdependent. The dosage and treatment regimen will also depend upon such factors as the specific Formula (I) compound used, the treatment indication, the ability of the Formula (I) compound to reach minimum inhibitory concentrations at the site of the metalloprotease to be inhibited, the personal attributes of the subject (such as weight), compliance with the treatment regimen, and the presence and severity of any side effects of the treatment.

Typically, for a human adult (weighing approximately 70 kilograms), from about 5 mg to about 3000 mg, more preferably from about 5 mg to about 1000 mg, more preferably from about 10 mg to about 100 mg, of Formula (I) compound are administered per day for systemic administration. It is understood that these dosage ranges are by way of example only, and that daily administration can be adjusted depending on the factors listed above.

A preferred method of administration for treatment of rheumatoid arthritis is oral or parenterally via intra-articular injection. As is known and practiced in the art, all formulations for parenteral administration must be sterile. For mammals, especially humans, (assuming an approximate body weight of 70 kilograms) individual doses of from about 10 mg to about 1000 mg are preferred.

A preferred method of systemic administration is oral. Individual doses of from about 10 mg to about 1000 mg, preferably from about 10 mg to about 300 mg are preferred.

Topical administration can be used to deliver the Formula (I) compound systemically, or to treat a subject locally. The amounts of Formula (I) compound to be topically administered depends upon such factors as skin sensitivity, type and location of the tissue to be treated, the composition and carrier (if any) to be administered, the particular Formula (I) compound to be administered, as well as the particular disorder to be treated and the extent to which systemic (as distinguished from local) effects are desired.

The inhibitors of the invention can be targeted to specific locations where the metalloprotease is accumulated by using targeting ligands. For example, to focus the inhibitors to metalloprotease contained in a tumor, the inhibitor is conjugated to an antibody or fragment thereof which is immunoreactive with a tumor marker as is generally understood in the preparation of immunotoxins in general. The targeting ligand can also be a ligand suitable for a receptor which is present on the tumor. Any targeting ligand which specifically reacts with a marker for the intended target tissue can be used. Methods for coupling the invention compound to the targeting ligand are well known and are similar to those described below for coupling to carrier. The conjugates are formulated and administered as described above.

For localized conditions, topical administration is preferred. For example, to treat ulcerated cornea, direct application to the affected eye may employ a formulation as eyedrops or aerosol. For corneal treatment, the compounds of the invention can also be formulated as gels, drops or ointments, or can be incorporated into collagen or a hydrophilic polymer shield. The materials can also be inserted as a contact lens or reservoir or as a subconjunctival formulation. For treatment of skin inflammation, the compound is applied locally and topically, in a gel, paste, salve or ointment. For treatment of oral diseases, the compound may be applied locally in a gel, paste, mouth wash, or implant. The mode of treatment thus reflects the nature of the condition and suitable formulations for any selected route are available in the art.

In all of the foregoing, of course, the compounds of the invention can be administered alone or as mixtures, and the compositions may further include additional drugs or excipients as appropriate for the indication.

Some of the compounds of the invention also inhibit bacterial metalloproteases. Some bacterial metalloproteases may be less dependent on the stereochemistry of the inhibitor, whereas substantial differences are found between diastereomers in their ability to inactivate the mammalian proteases. Thus, this pattern of activity can be used to distinguish between the mammalian and bacterial enzymes.

VII. EXAMPLES

Compound Preparation

The following abbreviations are used herein:

| MeOH: | methanol | $Et_3N$: | triethylamine |
|---|---|---|---|
| EtOAc: | ethylacetate | $Et_2O$: | diethylether |
| Ph: | phenyl | boc: | t-butyloxycarbonyl |
| DMF: | N,N-dimethylformamide | acac: | acetyl acetate |
| DME: | dimethoxyethane | dil.: | dilute |
| conc.: | concentrated | wrt.: | with respect to |
| DCC: | 1,3-Dicyclohexyl-carbodiimide | HOBT: | 1-Hydroxybenzotriazole |

The R groups used to illustrate the compound examples do not correlate to the respective R groups used to describe the various moieties of Formula (I). That is, for example, $R^1$ and $R^2$ used to describe Formula (I) in the Summary of the Invention section and Section II of the Detailed Description do not represent the same moieties as $R^1$ and $R^2$ in this Section VII.

Examples 1–18

The following chart shows the structure of compounds made according to the procedures described in Examples 1–16. In these examples, A of Formula (I) is a piperidine ring.

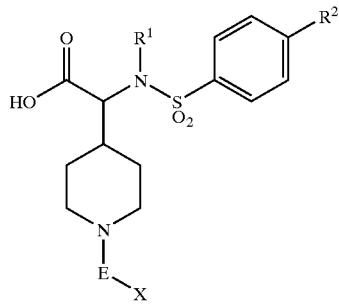

| Example | E | X | R¹ | R² |
|---|---|---|---|---|
| 1 | —C(=O)— | -N(morpholine)- | Me | —C₆H₄-4-OMe |
| 2 | —C(=O)— | -N(morpholine)- | —CH₂Ph | —C₆H₄-4-OMe |
| 3 | —C(=O)— | -N(morpholine)- | —Et | —C₆H₄-4-OMe |
| 4 | —C(=O)— | -N(morpholine)- | —Me | —C₆H₄-4-Br |
| 5 | —C(=O)O— | —CH₂CH₂OMe | —Me | —C₆H₄-4-OMe |
| 6 | —C(=O)O— | —CH₂CH₂OMe | —Et | —C₆H₄-4-OMe |
| 7 | —C(=O)O— | —CH₂CH₂OMe | —CH₂CH₂CH₂CH₃ | —C₆H₄-4-OMe |
| 8 | —C(=O)O— | —CH₂CH₂OMe | —CH₂CH₂OMe | —C₆H₄-4-OMe |
| 9 | —C(=O)O— | —CH₂CH₂OMe | —CH₂Ph | —C₆H₄-4-OMe |
| 10 | —C(=O)O— | —CH₂CH₂OMe | —CH₂CH₂Ph | —C₆H₄-4-OMe |
| 11 | —C(=O)O— | —CH₂CH₂OMe | —CH₂-2-pyridyl | —C₆H₄-4-OMe |
| 12 | —C(=O)O— | —CH₂CH₂OMe | —CH₂-3-pyridyl | —C₆H₄-4-OMe |
| 13 | —C(=O)O— | —CH₂CH₂OMe | Me | —C₆H₄-4-Br |
| 14 | —C(=O)O— | —CMe₃ | -CH₂CH₂-N(morpholine) | —C₆H₄-4-OMe |
| 15 | —C(=O)O— | —CMe₃ | —Me | —C₆H₄-4-F |
| 16 | —SO₂— | —CH₂Ph | —Me | —C₆H₄-4-OMe |
| 17 | —CH₂— | —CH₂Ph | —Me | —C₆H₄-4-OMe |

Example 1

[(4'-Methoxy-biphenyl-4-sulfonyl)-methyl-amino]-[1-(morpholine-4-carbonyl)-piperidin-4-yl]-acetic acid a) 4-(Benzyloxycarbonylamino-methoxycarbonyl-methylene)-piperidine-1-carboxylic acid tert-butyl ester. To a solution of 4-Boc-piperidone (30 g) and phosphonate (50 g) in dichloromethane (100 mL) cooled to 0° C. is added dropwise diazabicycloundecane (32.16 g). The resulting mixture is stirred at room temperature for 5 days. The solvent is removed under reduced pressure and the mixture is dissolved in EtOAc. The organic extracts are washed with water followed by brine, then dried (Na₂SO₄). The crude product obtained after evaporation of solvent is purified by chromatography on silica gel using 3/2 hexane/EtOAc to provide the desired product as a white solid.

b) 4-(Amino-methoxycarbonyl-methyl)-piperidine-1-carboxylic acid tert-butyl ester. 4-(Benzyloxycarbonylamino-methoxycarbonyl-methylene)-piperidine-1-carboxylic acid tert-butyl ester (49.1 g) is dissolved in methanol (100 mL) and 10% palladium on carbon (2.36 g) is added. The flask is flushed with hydrogen and the reaction mixture is stirred at room temperature for 12 hours. The reaction mixture is filtered through a Celite plug and the solvent is evaporated under reduced pressure to give the desired product which is used in the following reaction without purification.

c) 4-[(4'-Methoxy-biphenyl-4-sulfonylamino)-methoxycarbonyl-methyl]-piperidine-1-carboxylic acid tert-butyl ester. To a solution of 4-(amino-methoxycarbonyl-methyl)-piperidine-1-carboxylic acid tert-butyl ester triethylamine (3.05 g) followed by 4'-methoxy-biphenyl-4-sulfonyl chloride (6.19 g). The reaction mixture is stirred overnight at room temperature, washed sequentially with 1N hydrochloric acid, water, 5% aqueous sodium bicarbonate and brine, then dried ($Na_2SO_4$). The crude product obtained after evaporation of solvent is purified by chromatography on silica gel using 3/2 hexane/EtOAc to provide the desired product as a colorless solid.

d) (4'-Methoxy-biphenyl-4-sulfonylamino)-piperidin-4-yl-acetic acid methyl ester TFA salt. To a solution of 4-[(4'-methoxy-biphenyl-4-sulfonylamino)-methoxycarbonyl-methyl]-piperidine-1-carboxylic acid tert-butyl ester TFA salt (6.7 g) in dichloromethane (60 mL) is added trifluoroacetic acid (60 mL) and the reaction mixture is stirred at room temperature for 3 hours. The solvents are removed under reduced pressure and the crude product which solidifies upon standing is used in the next step without further purification.

e) (4'-Methoxy-biphenyl-4-sulfonylamino)-[1-(morpholine-4-carbonyl)-piperidin-4-yl]-acetic acid methyl ester. To a suspension of (4'-methoxy-biphenyl-4-sulfonylamino)-piperidin-4-yl-acetic acid methyl ester TFA salt (5.02 g) in dichloromethane (30 mL) is added triethylamine (2.5 mL) followed by morpholinecarbamoyl chloride (1.4 g) and the reaction mixture is stirred at room temperature for 4 hour. The solvents are removed under reduced pressure and the residue is diluted with ethyl acetate and washed successively with 1N hydrochloric acid, water, brine, and then dried ($Na_2SO_4$). The crude product obtained after evaporation of solvent is purified by crystallization from methanol to give the desired product as a colorless solid.

f) [(4'-Methoxy-biphenyl-4-sulfonyl)-methyl-amino]-[1-(morpholine-4-carbonyl)-piperidin-4-yl]-acetic acid methyl ester. To a solution of (4'-methoxy-biphenyl-4-sulfonylamino)-[1-(morpholine-4-carbonyl)-piperidin-4-yl]-acetic acid methyl ester (1.04 g) in dimethylformamide (8 mL) is added anhydrous cesium carbonate (0.75 g) followed by methyl iodide (0.85 mL) and the reaction mixture is stirred at room temperature overnight. The solvents are removed under reduced pressure and the residue is diluted with methylene chloride and washed successively with water, brine, and then dried ($Na_2SO_4$). The crude product obtained after evaporation of solvents is purified using RP-HPLC to give the desired product as a colorless solid.

g) [(4'-Methoxy-biphenyl-4-sulfonyl)-methyl-amino]-[1-(morpholine-4-carbonyl)-piperidin-4-yl]-acetic acid. To a solution of (4'-methoxy-biphenyl-4-sulfonyl)-methyl-amino)-[1-(morpholine-4-carbonyl)-piperidin-4-yl]-acetic acid methyl ester (323 mg) in tetrahydrofuran (10 mL) is added 50% sodium hydroxide (3 mL) and the reaction mixture is stirred at room temperature for 2 hours. The solvents are removed under reduced pressure and the residue is diluted with ethyl acetate and washed successively with water, brine, and then dried ($Na_2SO_4$). The crude product obtained after evaporation of solvents is purified using RP-HPLC to give the desired product as a colorless solid.

Example 2

[Benzyl-(4'-methoxy-biphenyl-4-sulfonyl)-amino]-[1-(morpholine-4-carbonyl)-piperidin-4-yl]-acetic acid a) [Benzyl-(4'-methoxy-biphenyl-4-sulfonyl)-amino]-[1-(morpholine-4-carbonyl)-piperidin-4-yl]-acetic acid methyl ester. To a solution of (4'-methoxy-biphenyl-4-sulfonylamino)-[1-(morpholine-4-carbonyl)-piperidin-4-yl]-acetic acid methyl ester (493 mg) in dimethylformamide (6 mL) is added anhydrous cesium carbonate (300 mg) followed by benzyl bromide (353 mg) and the reaction mixture is stirred at room temperature for 3 days. The solvents are removed under reduced pressure and the residue is diluted with ethyl acetate and washed successively with water, brine, and then dried ($Na_2SO_4$). The crude product obtained after evaporation of solvents is purified using RP-HPLC to give the desired product as a colorless solid.

b) [Benzyl-(4'-methoxy-biphenyl-4-sulfonyl)-amino]-[1-(morpholine-4-carbonyl)-piperidin-4-yl]-acetic acid. To a solution of [benzyl-(4'-methoxy-biphenyl-4-sulfonyl)-amino)-[1-(morpholine-4-carbonyl)-piperidin-4-yl]-acetic acid methyl ester (196 mg) in tetrahydrofuran (10 mL) is added 50% sodium hydroxide (4 mL) and the reaction mixture is stirred at room temperature overnight. The solvents are removed under reduced pressure and the residue is diluted with ethyl acetate and washed successively with water, brine, and then dried ($Na_2SO_4$). The crude product obtained after evaporation of solvents is purified using RP-HPLC to give the desired product as a colorless solid.

Example 3

Example 3 is prepared from Example 1e following the procedure described for Example 1 and using ethyl iodide in step 1f.

Example 4

Example 4 is prepared from Example 1b following the procedure described for Example 1 and using bromobiphenylsulfonyl chloride in step 1c.

Example 5

Example 5 is prepared from Example 1d following the procedure described for Example 1 and using methoxyethylchlorocarbonate in step 1e.

Example 6

Example 6 is prepared from Example 1d following the procedure described for Example 1 and using methoxyethylchlorocarbonate in step 1e and ethyl iodide in step 1f.

Example 7

Example 7 is prepared from Example 1d following the procedure described for Example 1 and using methoxyethylchlorocarbonate in step 1e and n-butyl iodide in step 1f.

Example 8

Example 8 is prepared from Example 1d following the procedure described for Example 1 and using methoxyethylchlorocarbonate in step 1e and 2-methoxyethyl chloride in step 1f.

Example 9

Example 9 is prepared from Example 1d following the procedure described for Example 1 and using methoxyethylchlorocarbonate in step 1e and benzyl bromide in step 1f.

Example 10

Example 10 is prepared from Example 1d following the procedure described for Example 1 and using methoxyethylchlorocarbonate in step 1e and phenylethyl bromide in step 1f.

Example 11

Example 11 is prepared from Example 1d following the procedure described for Example 1 and using methoxyethylchlorocarbonate in step 1e and 2-picolyl chloride in step 1f.

Example 12

Example 12 is prepared from Example 1d following the procedure described for Example 1 and using methoxyethylchlorocarbonate in step 1e and 3-picolyl chloride in step 1f.

Example 13

Example 13 is prepared from Example 1b following the procedure described for Example 1 and using 4-bromobiphenylsulfonyl chloride in step 1c and using methoxyethylcarbonate in step 1e.

Example 14

Example 14 is prepared from Example 1c following the procedure described for Example 14 and using 4-(2-chloroethyl)morpholine in step 1f.

Example 15

Example 15 is prepared from Example 1b following steps 1c, 1f and 1g as described for Example 1 and using fluorobiphenylsulfonyl chloride in step 1c.

Example 16

Example 16 is prepared from Example 1d following the procedure described for Example 1 and using benzylsulfonyl chloride in step 1e.

Example 17

[(4'-Methoxy-biphenyl-4-sulfonyl)-methyl-amino]-(1-phenethyl-piperidin-4-yl)-acetic Acid a) (4'-Methoxy-biphenyl-4-sulfonylamino)-(1-phenethyl-piperidin-4-yl)-acetic acid methyl ester: To a stirring solution of (4'-methoxy-biphenyl-4-sulfonylamino)-piperidin-4-yl-acetic acid methyl ester TFA salt (1d) (5.02 g, 9.15 mmol) in methanol (30 mL) is added phenylacetaldehyde (1.80 g, 15.0 mmol) and pyridine (1 mL). Borane pyridine complex (~8M $BH_3$, 2 mL) is then added drop wise and the solution is stirred at room temperature. After four hours, another 0.5 mL of $BH_3$-pyridine complex is added and the reaction is left to stir overnight. The solvent is removed under reduced pressure and the resulting white solid is taken up in ethyl acetate, washed with 1N hydrochloric acid, and water. The addition of 1N sodium hydroxide to the ethyl acetate resulted in the formation of a white precipitant that is filtered, washed with ethyl ether, and dried under vacuum to give the desired product.

b) [(4'-Methoxy-biphenyl-4-sulfonyl)-methyl-amino]-(1-phenethyl-piperidin-4-yl)-acetic acid: To a solution of (4'-methoxy-biphenyl-4-sulfonylamino)-(1-phenethyl-piperidin-4-yl)-acetic acid methyl ester (522 mg, 1.0 mmol) in N,N-dimethylformamide (5 mL) is added cesium carbonate (326 mg, 1.0 mmol), and methyl iodide (142 mg, 1.0 mmol). The mixture is stirred for four hours then diluted with water and extracted with dichloromethane. The organic extracts are combined, washed with brine, dried over sodium sulfate, filtered, and concentrated under vacuum to provide the desired product as a white solid.

c) [(4'-Methoxy-biphenyl-4-sulfonyl)-methyl-amino]-(1-phenethyl-piperidin-4-yl)-acetic acid methyl ester: To a stirring solution of [(4'-methoxy-biphenyl-4-sulfonyl)-methyl-amino](1-phenethyl-peridin-4-yl)-acetic acid (125 mg, 0.23 mmol) in tetrahydrofuran (4 mL), is added aqueous sodium hydroxide (50% w/w, 200 μL), methanol (0.5 mL). The slightly cloudy mixture is stirred overnight. The reaction is acidified with 1N hydrochloric acid, and extracted with dichloromethane. The organic phase is washed with brine, dried over sodium sulfate, filtered, and concentrated under vacuum. Crude product is purified using a prep RP-HPLC to give the desired product as a white glassy solid.

Examples 18–23

The following chart shows the structure of compounds made according to the procedures described in Examples 18–23 In this formula, A and $R^2$ of Formula (I) form the heterocycloalkyl containing A', which is a heteroatom in the ring.

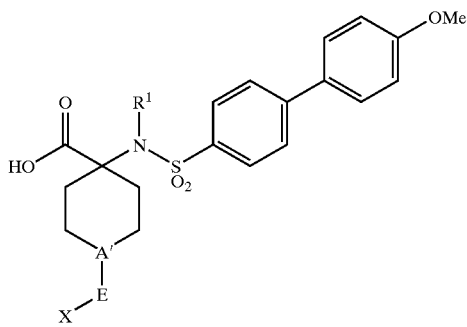

| Example | A' | E | X | $R^1$ |
|---|---|---|---|---|
| 18 | —O— | — | — | Me |

-continued

| Example | A' | E | X | R¹ |
|---|---|---|---|---|
| 19 | —N— | —C(=O)— | ⸻N(morpholine)⸻ | —Me |
| 20 | —N— | —C(=O)— | ⸻N(morpholine)⸻ | —CH₂Ph |
| 21 | —N— | —C(=O)— | —CH₂CH₂OMe | —CH₂Ph |
| 22 | —N— | —C(=O)O— | —CH₂CH₂OMe | —CH₂CH₂OMe |
| 23 | —N— | —CH₂— | —Ph | —CH₂Ph |

Example 18

4-[(4'-Methoxy-biphenyl-4-sulfonyl)-methyl-amino]-tetrahydro-pyran-4-carboxylic acid Example 18 is prepared by a method analogous to example 19 below.

Example 19
4-[(4'-Methoxy-biphenyl-4-sulfonyl)-methyl-amino]-1-(morpholine-4-carbonyl)-piperidine 4-carboxylic Acid a) 4-Amino-piperidine-1,4-dicarboxylic acid 1-tert-butyl ester 4-methyl ester. To a slurry of 4-amino-piperidine-1,4-dicarboxylic acid mono-tert-butyl ester (13.9 g) in methanol (150 mL) and tetrahydrofuran (100 mL) cooled to 0° C. is added dropwise over 4 hours 2 M trimethyl-silyldiazomethane in hexane (57 mL) followed by 4-nitrophenylsulfonyl chloride (2.0 g). The solvents are evaporated under vacuum and the crude product is used in the next step without further purification.

b) 4-(4'-Methoxy-biphenyl-4-sulfonylamino)-piperidine-1,4-dicarboxylic acid 1-tert-butyl ester 4-methyl ester. To a solution of 4-Amino-piperidine-1,4-dicarboxylic acid, 1-tert-butyl ester 4-methyl ester (155 mg) in dichloromethane (10 mL) is added triethylamine (125 mL) followed by p-methoxybiphenyl sulfonyl chloride (187 mg). The reaction mixture is stirred overnight at room temperature, washed with water and brine, then dried (MgSO₄). The crude product obtained after evaporation of solvent is purified by chromatography on silica gel using 4/1 hexane/EtOAc to provide the desired product as a colorless solid.

c) 4-(4'-Methoxy-biphenyl-4-sulfonylamino)-piperidine-4-carboxylic acid methyl ester TFA salt: The 4-(4'-Methoxy-biphenyl-4-sulfonylamino)-piperidine-1,4-dicarboxylic acid 1-tert-butyl ester 4-methyl ester (3.12 g, 6.19 mmol) is dissolved in CH₂Cl₂ (15 mL) in a 100 mL flask. To the solution is added anisole (1.35 mL, 12.4 mmol) followed by trifluoroacetic acid (15 mL) dropwise by syringe, and the mixture is stirred at 22° C. for 8 hours. The yellow reaction mixture is concentrated down to ca. 4–5 mL before adding it dropwise to a stirring solution of ether/hexanes (25 mL/475 mL). The precipitate is collected by filtration and washed with 10:90 ether/hexanes to give spectroscopically pure the TFA salt.

d) 4-(4'-Methoxy-biphenyl-4-sulfonylamino)-1-(morpholine-4-carbonyl)-piperidine-4-carboxylic acid methyl ester: The 4-(4'-methoxy-biphenyl-4-sulfonylamino)-piperidine-4-carboxylic acid methyl ester TFA salt (313 mg, 0.60 mmol) is stirred with CH₂Cl₂ (25 mL) in a 200 mL round bottom flask. Morpholine carbonyl chloride (85 mL, 0.72 mmol), and triethylamine (211 mL, 1.52 mmol) are added and the mixture is stirred at room temperature for 17 hours. The reaction is diluted with additional methylene chloride (50 mL) and extracted with water (3×75 mL). The extracts are rinsed with brine, dried over MgSO₄, filtered and concentrated in vacuo to leave a solid residue. Chromatography on silica gel using ethyl acetate/hexanes eluent gave the desired compound as a colorless solid.

e) 4-[(4'-Methoxy-biphenyl-4-sulfonyl)-methyl-amino]-1-(morpholine-4-carbonyl)-piperidine-4-carboxylic acid methyl ester: The 4-(4'-methoxy-biphenyl-4-sulfonylamino)-1-(morpholine-4-carbonyl)-piperidine-4-carboxylic acid methyl ester (65 mg, 0.13 mmol) is dissolved in DMF (2 mL) in a 10 mL conical reaction vial. To the solution is added cesium carbonate (82 mg, 0.25 mmol) followed by iodomethane (40 mL, 1.2 mmol) by syringe, and the mixture is stirred at room temperature for 16 hours. The reaction mixture is diluted with ethyl acetate (75 mL) and extracted four times with water (75 mL). The extracts are rinsed with brine, dried over MgSO₄, filtered and concentrated in vacuo to leave the desired compound as a crude solid residue.

f) 4-[(4'-Methoxy-biphenyl-4-sulfonyl)-methyl-amino]-1-(morpholine-4-carbonyl)-piperidine-4-carboxylic acid:
The 4-[(4'-methoxy-biphenyl-4-sulfonyl)-methyl-amino]-1-(morpholine-4-carbonyl)-piperidine-4-carboxylic acid methyl ester (215 mg, 0.49 mmol) is dissolved in THF (5 mL) in a 50 mL round bottom flask. A solution of lithium hydroxide monohydrate (210 mg, 5.0 mmol) in 5 mL of water is added and the mixture is stirred in an oil bath at 70° C. for 4 hours. After removal of most of the THF under reduced pressure left the aqueous layer which is washed twice with diethyl ether. The aqueous layer is diluted with water (50 mL) and ethyl acetate (100 mL) and placed into an erlenmeyer flask. With stirring, 6N HCl followed by 1N HCl are added dropwise to achieve pH of 2–3 in the aqueous layer. The layers are separated and the aqueous layer is extracted with additional ethyl acetate. The extracts are rinsed with brine, dried over MgSO$_4$, filtered and concentrated in vacuo to leave a solid residue. Purification by preparative HPLC gave the desired compound as a colorless solid.

Example 20

Example 20 is prepared from Example 19d following the procedure described for Example 19, substituting benzyl bromide (1.5 equiv) in place of the methyl iodide in step 19e.

Example 21

Example 21 is prepared from Example 19c following the procedure described for Example 19, substituting methoxyethylchlorocarbonate in step 19d and benzyl bromide in step 19e.

Example 22

Example 22 is prepared from Example 19c following the procedure described for Example 19, substituting methoxyethylchlorocarbonate in step 19d and methoxyethyl bromide in step 19e.

Example 23

Example 23 is prepared from Example 19c following the procedure described for Example 19, substituting benzyl bromide in step 19d and benzyl bromide in step 19e.

Examples 24–34

The following chart shows the structure of compounds made according to the procedures described in Examples 24–34.

| Example | E | X | R$^1$ | R$^2$ |
|---|---|---|---|---|
| 24 | —C(=O)— | N-morpholine | Me | —C$_6$H$_4$-4-OMe |
| 25 | —C(=O)— | N-morpholine | —CH$_2$Ph | —C$_6$H$_4$-4-OMe |
| 26 | —C(=O)— | N-morpholine | —Et | —C$_6$H$_4$-4-OMe |
| 27 | —C(=O)— | N-morpholine | —Me | —C$_6$H$_4$-4-Br |
| 28 | —C(=O)O— | —CH$_2$CH$_2$OMe | Me | —C$_6$H$_4$-4-OMe |
| 29 | —C(=O)O— | —CH$_2$CH$_2$OMe | —Et | —C$_6$H$_4$-4-OMe |
| 30 | —C(=O)O— | —CH$_2$CH$_2$OMe | —CH$_2$Ph | —C$_6$H$_4$-4-OMe |
| 31 | —C(=O)O— | —CMe$_3$ | —Me | —C$_6$H$_4$-4-OMe |
| 32 | —C(=O)O— | —CMe$_3$ | —Me | —C$_6$H$_4$-4-F |
| 33 | —SO$_2$— | —CH$_2$Ph | —Me | —C$_6$H$_4$-4-OMe |
| 34 | —CH$_2$— | —CH$_2$Ph | —Me | —C$_6$H$_4$-4-OMe |

Example 24

N-Hydroxy-2-[(4'-methoxy-biphenyl-4-sulfonyl)-methyl-amino]-2-[1-(morpholine-4carbonyl)-piperidin-4-yl]-acetamide. [(4'-Methoxy-biphenyl-4-sulfonyl)-methyl-amino]-[1-(morpholine-4-yl)-piperidin-4-yl]-acetic acid methyl ester (311 mg) is treated with a methanolic solution of hydroxylamine (1.76 M, 3 mL) and the reaction is stirred for 12 hours at room temperature. The reaction mixture is concentrated under reduced pressure, diluted with ethyl acetate and washed successively with 1N hydrochloric acid, water, brine, and then dried ($Na_2SO_4$). The product obtained after evaporation of solvents is purified using RP-HPLC to give the desired product as a colorless solid.

Examples 25–34

Examples 25–34 are prepared from the corresponding methyl esters following the procedure described for Example 24.

Examples 35–39

The following chart shows the structure of compounds made according to the procedures described in Examples 36–40. With reference to Formula (I), the compounds are those where $R^1$ is —OH, n is 0, $R^2$ is H and A is the X-containing ring depicted below.

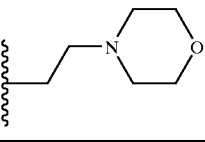

| Example | X | $R^1$ | $R^2$ |
|---|---|---|---|
| 35 | O | Me | —$C_6H_4$-4-OMe |
| 36 | O | —$CH_2$Ph | —$C_6H_4$-4-OMe |
| 37 | O | —$CH_2CH_2$OMe | —$C_6H_4$-4-OMe |
| 38 | O | —$CH_2$-3-pyridyl | —$C_6H_4$-4-OMe |
| 39 | O | ⸺CH₂CH₂-N(morpholine) | —$C_6H_4$-4-OMe |

Example 35

[(4'-Methoxy-phenyl-4-sulfonyl)-methyl-amino]-(tetrahydro-pyran-4-yl)-acetic acid a) Benzyloxycarbonylamino-(tetrahydro-pyran-4-ylidene)-acetic acid methyl ester. In a 50 mL round bottom flask is prepared a solution in acetonitrile (10 mL) of N-(benzyloxycarbonyl)-a-phosphonoglycine trimethyl ester (1000 mg, 3.02 mmol) to which is added 1,8-diazabicylco[5.4.0]undec-7-ene (0.45 mL, 3.02 mmol). After allowing the mixture to stir for 10 minutes, the tetrahydro-4H-pyran-4-one (299 mg, 2.95 mmol) is added and the reaction mixture is stirred for 2 days. The solution is then diluted with EtOAc (75 mL) and subsequently washed with 1N $H_2SO_4$ solution. The solution is then dried by washing with brine and stirring with $MgSO_4$. After filtration and concentration of the filtrate by rotoevaporation, the dark reddish brown oil is diluted with ethyl acetate and hexane (1:1) and filtered through a plug of silica gel to remove excess phosphorylglycine ester using 1:1 ethyl acetate/hexane eluent. The solvent is removed in vacuo to give the desired compound.

b) Amino-(tetrahydro-pyran-4-yl)-acetic acid methyl ester. The benzyloxycarbonylamino-(tetrahydro-pyran-4-ylidene)-acetic acid methyl ester (361 mg, 1.18 mmol) is added to a Parr hydrogenation bottle with anhydrous methanol (6 mL) and the solution is degassed with argon for 10 minutes. To the vessel is then added 5% palladium/carbon catalyst. The solvent is then placed under a 3 Atm blanket of hydrogen and shaken overnight. The catalyst is then removed by filtration through Celite. Removal of organic solvent under reduced pressure and subsequent drying in vacuo gives an oily residue, for which NMR and mass spectrometric analysis show that the desired ester has been prepared. The crude product is used as is without further purification.

c) (4'-Methoxy-biphenyl-4-sulfonylamino)-(tetrahydro-pyran-4-yl)-acetic acid methyl ester. In a 100 mL round bottom flask is dissolved under nitrogen the crude amino-(tetrahydro-pyran-4-yl)-acetic acid methyl ester (288 mg, 1.17 mmol) in anhydrous $CH_2Cl_2$ (8 mL). After addition of triethylamine (330 mL, 2.35 mmol), p-methoxybiphenyl sulfonyl chloride (499 mg, 1.76 mmol) is added and the solution stirred overnight at room temperature. The reaction mixture is washed with water and brine and dried over $MgSO_4$. The crude material obtained after removal of solvents is purified by flash chromatography (40:60 ethyl acetate:hexanes solvent) to give the desired product as a white solid d) [(4'-Methoxy-biphenyl-4-sulfonyl)-methyl-amino]-(tetrahydro-pyran-4-yl)-acetic acid methyl ester: The (4'-methoxy-biphenyl-4-sulfonylamino)-(tetrahydro-pyran-4-yl)-acetic acid methyl ester (231 mg, 0.55 mmol) is dissolved in DMF (4 mL) in a 10 mL conical reaction vial. To the solution is added cesium carbonate (359 mg, 1.12 mmol) followed by methyl iodide (343 ml, 5.51 mmol) by syringe and the mixture is stirred at 67° C. for 16 hours. The reaction mixture is diluted with ethyl acetate (100 mL) and extracted four times with water (75 mL). Rinsed with brine and dried over $MgSO_4$, filtered and concentrated in vacuo to leave the desired compound as a crude solid residue.

e) [(4'-Methoxy-biphenyl-4-sulfonyl)-methyl-amino]-(tetrahydro-pyran-4-yl)-acetic acid: The [(4'-methoxy-biphenyl-4-sulfonyl)-methyl-amino]-(tetrahydro-pyran-4-yl)-acetic acid methyl ester (215 mg, 0.49 mmol) is dissolved in THF (5 mL) in a 50 mL round bottom flask. A solution of lithium hydroxide monohydrate (210 mg, 5.0 mmole) in 5 mL of water is added and the mixture is stirred in an oil bath at 70° C. for 4 hours. After removal of most of the THF by rotoevaporation, the aqueous layer is washed twice with diethyl ether. The aqueous layer is diluted with water (50 mL) and ethyl acetate (100 mL) and placed into an erlenmeyer flask. With stirring, 6N HCl followed by 1N HCl are added dropwise to achieve pH of 2–3 in the aqueous layer. The layers are separated and the aqueous layer is extracted with additional ethyl acetate. Rinsed with brine and dried over $MgSO_4$, filtered and concentrated in vacuo to leave a solid residue. Purification by preparative HPLC gives the desired compound as a colorless solid.

Example 36

Example 36 is prepared from Example 35c following the procedure described for Example 35, substituting benzyl bromide in step 35d.

Example 37

Example 37 is prepared from Example 35c following the procedure described for Example 35, substituting methoxyethyl bromide in step 35d.

Example 38

Example 38 is prepared from Example 35c following the procedure described for Example 35, substituting 3-picolyl bromide in step 35d.

Example 39

Example 39 is prepared from Example 35c following the procedure described for Example 35, substituting morpholinylethyl bromide in step 35d.

VIII. EXAMPLES

Compositions and Methods of Use

The compounds of the invention are useful to prepare compositions for the treatment of ailments associated with unwanted MP activity. The following composition and method examples do not limit the invention, but provide guidance to the skilled artisan to prepare and use the compounds, compositions and methods of the invention. In each case other compounds within the invention may be substituted for the example compound shown below with similar results. The skilled practitioner will appreciate that the examples provide guidance and may be varied based on the condition being treated and the patient.

The following abbreviations are used in this section:

EDTA: ethylenediaminetetracetic acid
SDA: synthetically denatured alcohol
USP: United States Pharmacopoeia

Example A

A tablet composition for oral administration, according to the present invention, is made comprising:

| Component | Amount |
| --- | --- |
| The compound of Example 30 | 15 mg |
| Lactose | 120 mg |
| Maize Starch | 70 mg |
| Talc | 4 mg |
| Magnesium Stuart | 1 mg |

A human female subject weighing 60 kg (132 lbs), suffering from rheumatoid arthritis, is treated by a method of this invention. Specifically, for 2 years, a regimen of three tablets per day is administered orally to said subject.

At the end of the treatment period, the patient is examined and is found to have reduced inflammation, and improved mobility without concomitant pain.

Example B

A capsule for oral administration, according to the present invention, is made comprising:

| Component | Amount (% w/w) |
| --- | --- |
| The compound of Example 2 | 15% |
| Polyethylene glycol | 85% |

A human male subject weighing 90 kg (198 lbs.), suffering from osteoarthritis, is treated by a method of this invention. Specifically, for 5 years, a capsule containing 70 mg of the compound of Example 3 is administered daily to said subject.

At the end of the treatment period, the patient is examined via x-ray, arthroscopy and/or MRI, and found to have no further advancement of erosion/fibrillation of the articular cartilage.

Example C

A saline-based composition for local administration, according to the present invention, is made comprising:

| Component | Amount (% w/w) |
| --- | --- |
| The compound of Example 10 | 5% |
| Polyvinyl alcohol | 15% |
| Saline | 80% |

A patient having deep corneal abrasion applies the drop to each eye twice a day. Healing is speeded, with no visual sequelae.

Example D

A topical composition for local administration, according to the present invention, is made comprising:

| Component | Composition (% w/v) |
| --- | --- |
| The compound of Example 20 | 0.20 |
| Benzalkonium chloride | 0.02 |
| Thimerosal | 0.002 |
| d-Sorbitol | 5.00 |
| Glycine | 0.35 |
| Aromatics | 0.075 |
| Purified water | q.s. |
| Total = | 100.00 |

A patient suffering from chemical burns applies the composition at each dressing change (b.i.d.). Scarring is substantially diminished.

Example E

An inhalation aerosol composition, according to the present invention, is made comprising:

| Component | Composition (% w/v) |
| --- | --- |
| Compound of Example 17 | 5.0 |
| Alcohol | 33.0 |
| Ascorbic acid | 0.1 |
| Menthol | 0.1 |

| Component | Composition (% w/v) |
|---|---|
| Sodium Saccharin | 0.2 |
| Propellant (F12, F114) | q.s. |
| Total = | 100.0 |

An asthma sufferer sprays 0.01 mL via a pump actuator into the mouth while inhaling. Asthma symptoms are diminished.

Example F

A topical opthalmic composition, according to the present invention, is made comprising:

| Component | Composition (% w/v) |
|---|---|
| Compound of Example 29 | 0.10 |
| Benzalkonium chloride | 0.01 |
| EDTA | 0.05 |
| Hydroxyethylcellulose (NATROSOL M) | 0.50 |
| Sodium metabisulfite | 0.10 |
| Sodium chloride (0.9%) | q.s. |
| Total = | 100.0 |

A human male subject weighing 90 kg (198 lbs), suffering from corneal ulcerations, is treated by a method of this invention. Specifically, for 2 months, a saline solution containing 10 mg of the compound of Example 16 is administered to said subject's affected eye twice-daily.

Example G

A composition for parenteral administration is made comprising:

| Component | Amount |
|---|---|
| The compound of Example 26 | 100 mg/mL carrier |
| Carrier: | |
| Sodium citrate buffer with (percent by weight of carrier): | |
| lecithin | 0.48% |
| carboxymethylcellulose | 0.53 |
| povidone | 0.50 |
| methyl paraben | 0.11 |
| propyl paraben | 0.011 |

The above ingredients are mixed, forming a suspension. Approximately 2.0 mL of the suspension is administered, via injection, to a human subject with a premetastatic tumor. The injection site juxtaposes the tumor. This dosage is repeated twice daily, for approximately 30 days. After 30 days, symptoms of the disease subside, and dosage is gradually decreased to maintain the patient.

Example H

A mouthwash composition is prepared:

| Component | % w/v |
|---|---|
| The compound of Example 3 | 3.00 |
| SDA 40 Alcohol | 8.00 |
| Flavor | 0.08 |
| Emulsifier | 0.08 |
| Sodium Fluoride | 0.05 |
| Glycerin | 10.00 |
| Sweetener | 0.02 |
| Benzoic acid | 0.05 |
| Sodium hydroxide | 0.20 |
| Dye | 0.04 |
| Water | balance to 100% |

A patient with gum disease uses 1 mL of the mouthwash thrice daily to prevent further oral degeneration.

Example I

A lozenge composition is prepared:

| Component | % w/v |
|---|---|
| The compound of Example 19 | 0.01 |
| Sorbitol | 17.50 |
| Mannitol | 17.50 |
| Starch | 13.60 |
| Sweetener | 1.20 |
| Flavor | 11.70 |
| Color | 0.10 |
| Corn Syrup | balance to 100% |

A patient uses the lozenge to prevent loosening of an implant in the maxilla.

Example J

| Chewing Gum Composition | |
|---|---|
| Component | w/v % |
| The compound of Example 6 | 0.03 |
| Sorbitol crystals | 38.44 |
| Paloja-T gum base | 20.00 |
| Sorbitol (70% aqueous solution) | 22.00 |
| Mannitol | 10.00 |
| Glycerine | 7.56 |
| Flavor | 1.00 |

A patient chews the gum to prevent loosening of dentures.

Example K

| Components | w/v % |
|---|---|
| Compound of Example 33 | 4.0 |
| USP Water | 50.656 |
| Methylparaben | 0.05 |
| Propylparaben | 0.01 |
| Xanthan Gum | 0.12 |
| Guar Gum | 0.09 |
| Calcium carbonate | 12.38 |

| Components | w/v % |
|---|---|
| Antifoam | 1.27 |
| Sucrose | 15.0 |
| Sorbitol | 11.0 |
| Glycerin | 5.0 |
| Benzyl Alcohol | 0.2 |
| Citric Acid | 0.15 |
| Coolant | 0.00888 |
| Flavor | 0.0645 |
| Colorant | 0.0014 |

The composition is prepared by first mixing 80 kg of glycerin and all of the benzyl alcohol and heating to 65° C., then slowly adding and mixing together methylparaben, propylparaben, water, xanthan gum, and guar gum. Mix these ingredients for about 12 minutes with a Silverson in-line mixer. Then slowly add in the following ingredients in the following order: remaining glycerin, sorbitol, antifoam C, calcium carbonate, citric acid, and sucrose. Separately combine flavors and coolants and then slowly add to the other ingredients. Mix for about 40 minutes. The patient takes the formulation to prevent flare up of colitis.

Example L

An obese human female subject, who is determined to be prone to osteoarthritis, is administered the capsule described in Example B to prevent the symptoms of osteoarthritis. Specifically, a capsule is administered daily to the subject.

The patient is examined via x-ray, arthroscopy and/or MRI, and found to have no significant advancement of erosion/fibrillation of the articular cartilage.

Example M

A human male subject weighing 90 kg (198 lbs.), who suffers a sports injury, is administered the capsule described in Example B to prevent the symptoms of osteoarthritis. Specifically, a capsule is administered daily to the subject.

The patient is examined via x-ray, arthroscopy and/or MRI, and found to have no significant advancement of erosion/fibrillation of the articular cartilage.

All references described herein are hereby incorporated by reference.

While particular embodiments of the subject invention have been described, it will be obvious to those skilled in the art that various changes and modifications of the subject invention can be made without departing from the spirit and scope of the invention. It is intended to cover, in the appended claims, all such modifications that are within the scope of this invention.

What is claimed is:

1. A compound having a structure according to Formula (I):

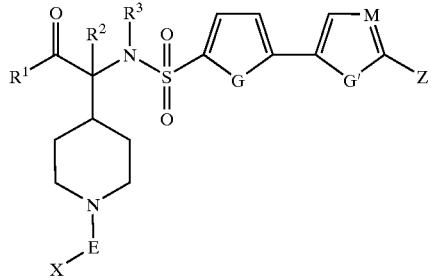

wherein:
(A) $R^1$ is —OH;
(B) $R^2$ is selected from hydrogen, alkyl, alkenyl, alkynyl, heteroalkyl, haloalkyl, cycloalkylalkyl, heterocycloalkylalkyl, arylalkyl and heteroarylalkyl;
(C) $R^3$ is selected from alkyl, alkenyl, alkynyl, heteroalkyl, haloalkyl, cycloalkyl, heterocycloalkyl, arylalkyl and heteroarylalkyl;
(D) E is selected from a covalent bond, $C_1$–$C_4$ alkyl, —C(=O)—, —C(=O)O—, —C(=O)N($R^4$)—, —$SO_2$— and —C(=S)N($R^4$)—, where $R^4$ is selected from hydrogen, alkyl, alkenyl, alkynyl, heteroalkyl, haloalkyl, cycloalkyl, heterocycloalkyl, aryl, arylalkyl, heteroaryl and heteroarylalkyl; or $R^4$ and X join to form a ring as described in (E) (2);
(E) (1) X is selected from hydrogen, alkyl, alkenyl, alkynyl, heteroalkyl, haloalkyl, aryl, arylalkyl, heteroaryl, heteroarylalkyl, cycloalkyl and heterocycloalkyl; or (2) X and $R^4$ join to form a substituted or unsubstituted, monocyclic heterocycloalkyl having from 3 to 8 ring atoms of which 1 to 3 are heteroatoms;
(F) G is —C($R^5$)=C($R^{5'}$)—, where $R^5$ and $R^{5'}$ each is hydrogen;
(G) G' is selected from —S—, —O—, —N($R^6$)—, —C($R^6$)=C($R^{6'}$)—, —N=C($R^6$)—, and —N=N—, where $R^{6'}$ and $R^6$ each is independently selected from hydrogen, alkyl, alkenly, alkynyl, heteroalkyl, heteroaryl, cycloalkyl and heterocycloalkyl;
(H) M is selected from —CH— and —N—; and
(I) Z is —(CR$^7$R$^{7'}$)$_a$—L—$R^8$, where:
(1) a is from 0 to about 4;
(2) each $R^7$ and $R^{7'}$ is independently selected from hydrogen, alkyl, alkenyl, alkynyl, aryl, heteroalkyl, heteroaryl, cycloalkyl, heterocycloalkyl, halogen, haloalkyl, hydroxy and alkoxy;
(3) L is selected from a covalent bond, —O—, —SO$_b$—, —C(=O)—, —C(=O)N($R^9$)—, —N($R^9$)— and —N($R^9$)C(=O)—; where b is from 0 to 2 and $R^9$ is selected from hydrogen, alkyl, alkenyl, alkynyl, aryl, heteroaryl, heteroalkyl, heteroaryl, cycloalkyl, heterocycloalkyl and haloalkyl; or $R^7$ and $R^9$, together with the atoms to which they are bonded, join to form an optionally substituted heterocyclic ring containing from 5 to 8 atoms of which 1 to 3 are heteroatoms; and
(4) $R^8$ is selected from hydrogen, alkyl, alkenyl, alkynyl, halogen, heteroalkyl, haloalkyl, aryl, heteroaryl, cycloalkyl and heterocycloalkyl; or $R^8$ and $R^9$, together with the atoms to which they are bonded, join to form an optionally substituted heterocyclic ring containing from 5 to 8 atoms of which 1 to 3 are heteroatoms;

or an optical isomer, diastereomer or enantiomer for Formula (I), or a pharmaceutically-acceptable salt, or biohydrolyzable amide, ester, or imide thereof.

2. The compound of claim 1 wherein $R^2$ is hydrogen or alkyl.

3. The compound of claim 1 wherein E is selected from a bond, $C_1$-$C_4$ alkyl, —C(=O)—, —C(=O)O—, —C(=O)N($R^4$)— and —$SO_2$—.

4. The compound of claim 3 wherein E is selected from $C_1$-$C_2$ alkyl, —C(=O)—, —C(=O)O— and —C(=O)N($R^4$)—.

5. The compound of claim 1 wherein X is selected from hydrogen, alkyl, heteroalkyl, aryl, arylalkyl, heteroaryl, heteroarylalkyl, cycloalkyl and heterocycloalkyl.

6. The compound of claim 1 wherein X and $R^4$ join to form a substituted or unsubstituted, monocyclic heterocycloalkyl having from 3 to 8 ring atoms and 1 to 3 ring heteroatoms.

7. The compound of claim 1 wherein $R^3$ is selected from alkyl, heteroalkyl, heterocycloalkyl, arylalkyl and heteroarylalkyl.

8. The compound of claim 1 wherein a is 0 and L is selected from —O— and —S—.

9. The compound of claim 8 wherein $R^8$ is selected from halogen, lower alkyl, lower heteroalkyl and aryl.

10. The compound of claim 1 selected from the group consisting of:

[(4'-Methoxy-biphenyl-4-sulfonyl)-methyl-amino]-[1-(morpholine-4-carbonyl)-piperidin-4-yl]-acetic acid;

[Benzyl-(4'-methoxy-biphenyl-4-sulfonyl)-amino]-[1-(morpholine-4-carbonyl)-piperidin-4-yl]-acetic acid;

[Ethyl-(4'-methoxy-biphenyl-4-sulfonyl)-amino]-[1-(morpholine-4-carbonyl)-piperidin-4-yl]-acetic acid;

[(4'-Bromo-biphenyl-4-sulfonyl)-methyl-amino]-[1-(morpholine-4-carbonyl)-piperidin-4-yl]-acetic acid;

4-{Carboxy-[(4'-methoxy-biphenyl-4-sulfonyl)-methyl-amino]-methyl}-piperidine-1-carboxylic acid 2-methoxy-ethyl ester;

4-{Carboxy-[ethyl-(4'-methoxy-biphenyl-4-sulfonyl)-amino]-methyl}-piperidine-1-carboxylic acid 2-methoxy-ethyl ester;

4-{[Butyl-(4'-methoxy-biphenyl-4-sulfonyl)-amino]-carboxy-methyl}-piperidine-1-carboxylic acid 2-methoxy-ethyl ester;

4-{Carboxy-[(4'-methoxy-biphenyl-4-sulfonyl)-(2-methoxy-ethyl)-amino]-methyl}-piperidine-1-carboxylic acid 2-methoxy-ethyl ester;

4-{[Benzyl-(4'-methoxy-biphenyl-4-sulfonyl)-amino]-carboxy-methyl}-piperidine-1-carboxylic acid 2-methoxy-ethyl ester;

4-{Carboxy-[(4'-methoxy-biphenyl-4-sulfonyl)-phenethyl-amino]-methyl}-piperidine-1-carboxylic acid 2-methoxy-ethyl ester;

4-{Carboxy-[(4'-methoxy-biphenyl-4-sulfonyl)-pyridin-2-ylmethyl-amino]-methyl}-piperidine-1-carboxylic acid 2-methoxy-ethyl ester;

4-{Carboxy-[(4'-methoxy-biphenyl-4-sulfonyl)-pyridin-3-ylmethyl-amino]-methyl}-piperidine-1-carboxylic acid 2-methoxy-ethyl ester;

4-{Carboxy-[(4'-methoxy-biphenyl-4-sulfonyl)-(2-morpholin-4-yl-ethyl)-amino]-methyl}-piperidine-1-carboxylic acid tert-butyl ester;

4-{Carboxy-[(4'-fluoro-biphenyl-4-sulfonyl)-methyl-amino]-methyl}-piperidine-1-carboxylic acid tert-butyl ester;

[(4'-Methoxy-biphenyl-4-sulfonyl)-methyl-amino]-(1-phenylmethanesulfonyl-piperidin-4-yl)-acetic acid;

[(4'-Methoxy-biphenyl-4-sulfonyl)-methyl-amino]-(1-phenethyl-piperidin-4-yl)-acetic acid;

4-[(4'-Methoxy-biphenyl-4-sulfonyl)-methyl-amino]-1-(morpholine-4-carbonyl)-piperidine-4-carboxylic acid;

4-[Benzyl-(4'-methoxy-biphenyl-4-sulfonyl)-amino]-1-(morpholine-4-carbonyl)-piperidine-4-carboxylic acid;

4-[Benzyl-(4'-methoxy-biphenyl-4-sulfonyl)-amino]-piperidine-1,4-dicarboxylic acid mono-(2-methoxy-ethyl) ester;

4-[Benzyl-(4'-methoxy-biphenyl-4-sulfonyl)-amino]-piperidine-1,4-dicarboxylic acid mono-(2-methoxy-ethyl) ester;

4-[(4'-Methoxy-biphenyl-4-sulfonyl)-(2-methoxy-ethyl)-amino]-piperidine-1,4-dicarboxylic acid mono-(2-methoxy-ethyl) ester;

1-Benzyl-4-[benzyl-(4'-methoxy-biphenyl-4-sulfonyl)-amino]-piperidine-4-carboxylic acid;

4-{Hydroxycarbamoyl-[(4'-methoxy-biphenyl-4-sulfonyl)-methyl-amino]-methyl}-piperidine-1-carboxylic acid 2-methoxy-ethyl ester;

4-{[Ethyl-(4'-methoxy-biphenyl-4-sulfonyl)-amino]-hydroxycarbamoyl-methyl}-piperidine-1-carboxylic acid 2-methoxy-ethyl ester;

4-{Hydroxycarbamoyl-[(4'-methoxy-biphenyl-4-sulfonyl)-phenethyl-amino]-methyl}-piperidine-1-carboxylic acid 2-methoxy-ethyl ester;

4-{Hydroxyarbamoyl-[(4'-methoxy-biphenyl-4-sulfonyl)-methyl-amino]-methyl}-piperidine-1-carboxylic acid tert-butyl ester; and 4-{[(4'-Fluoro-biphenyl-4-sulfonyl)-methyl-amino]-hydroxycarbamoyl-methyl}-piperidine-1-carboxylic acid tert-butyl ester.

11. A pharmaceutical composition comprising:

(a) a safe and effective amount of a compound of claim 1; and (b) a pharmaceutically-acceptable carrier.

12. A pharmaceutical composition comprising:

(a) a safe and effective amount of a compound of claim 10; and (b) a pharmaceutically-acceptable carrier.

13. A method for treating a disease associated with unwanted metalloprotease activity in a mammalian subject, the method comprising administering to said subject a safe and effective amount of a compound of claim 1.

14. A method for treating a disease associated with unwanted metalloprotease activity in a mammalian subject, the method comprising administering to said subject a safe and effective amount of a compound of claim 10.

15. A method for treating a disorder modulated by metalloproteases, wherein the disorder is chosen from the group consisting of arthritis, cardiovascular disorders, skin disorders, ocular disorders, inflammation and gum disease, the method comprising administering to a mammal in need of such treatment a safe and effective amount of a metalloprotease inhibitor according to claim 1.

16. The method for treating a disorder according to claim 15, wherein the disorder is arthritis, and is chosen from the group consisting of osteoarthritis and rheumatoid arthritis.

17. The method for treating a disorder according to claim 15, wherein the disorder is a cardiovascular disorder chosen from the group consisting of dilated cardiomyopathy, congestive heart failure, atherosclerosis, plaque rupture, reperfusion injury, ischemia, chronic obstructive pulmonary disease, angioplasty restenosis, and aortic aneurysm.

18. The method for the treating a disorder according to claim 15, wherein the disorder is an ocular disorder, and is chosen from the group consisting of corneal ulceration, lack of corneal healing, macular degeneration, retinopathy, and pterygium.

19. The method for treating a disorder according to claim 15, wherein the disorder is gum disease, and is chosen from the group consisting of periodontal disease and gingivitis.

20. The method for treating a disorder according to claim 15, wherein the disorder is a skin a disorder chosen from the group consisting of wrinkle repair and prevention, U.V. skin damage, epidermolysis bullosa, psoriasis, sclerodema, atopic dermatitis, and scarring.

21. A method for treating inflammatory conditions according to claim 15, wherein said inflammatory condition is chosen from the group consisting of inflammatory bowel disease, Crohn's Disease, ulcerative colitis, pancreatitis, diverticulitis, acne inflammation, bronchitis, arthritis, and asthma.

22. A method of preventing or treating a myocardial infarction/progressive ventricular dilation comprising administering to a mammal in need of such treatment, a safe and effective amount of a compound of having a structure according to claim 1.

* * * * *